US008119691B2

(12) United States Patent
Serhan et al.

(10) Patent No.: US 8,119,691 B2
(45) Date of Patent: *Feb. 21, 2012

(54) METHOD FOR TREATING AIRWAY HYPER-RESPONSIVENESS WITH LIPOXIN ANALOGS

(75) Inventors: Charles N. Serhan, Needham, MA (US); Bruce D. Levy, West Roxbury, MA (US)

(73) Assignee: National Institutes of Health (NIH), Bethesda, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/281,132

(22) Filed: Nov. 17, 2005

(65) Prior Publication Data

US 2006/0079577 A1    Apr. 13, 2006

Related U.S. Application Data

(62) Division of application No. 10/289,654, filed on Nov. 6, 2002, now abandoned.

(60) Provisional application No. 60/391,049, filed on Jun. 24, 2002, provisional application No. 60/338,862, filed on Nov. 6, 2001.

(51) Int. Cl.
*A61K 31/195* (2006.01)
*A61K 31/20* (2006.01)

(52) U.S. Cl. ...................... 514/562; 514/560

(58) Field of Classification Search ............... 514/560, 514/562
See application file for complete search history.

(56) References Cited

U.S. PATENT DOCUMENTS

| | | | |
|---|---|---|---|
| 4,560,514 A | 12/1985 | Samuelsson et al. | |
| 4,576,758 A | 3/1986 | Morris | |
| 4,780,281 A | 10/1988 | Marnett et al. | |
| 5,049,681 A | 9/1991 | Sato | |
| 5,079,261 A | 1/1992 | Serhan et al. | |
| 5,322,699 A | 6/1994 | Wright et al. | |
| 5,441,951 A * | 8/1995 | Serhan | 514/513 |
| 5,648,512 A | 7/1997 | Serhan | |
| 5,650,435 A | 7/1997 | Madara et al. | |
| 5,837,699 A * | 11/1998 | Sequeira et al. | 514/169 |
| 5,998,487 A | 12/1999 | Brahms et al. | |
| 6,177,468 B1 | 1/2001 | Madara et al. | |
| 6,353,026 B1 | 3/2002 | Serhan | |
| 6,387,953 B1 | 5/2002 | Serhan | |
| 6,495,596 B1 * | 12/2002 | Keller | 514/533 |
| 6,659,282 B2 | 12/2003 | Serhan | |
| 6,703,423 B2 | 3/2004 | Serhan | |
| 6,710,084 B2 | 3/2004 | Serhan | |
| 6,831,186 B2 * | 12/2004 | Bauman et al. | 548/253 |
| 2001/0031882 A1 | 10/2001 | Serhan | |

FOREIGN PATENT DOCUMENTS

| | | |
|---|---|---|
| WO | WO 94/29262 | 12/1994 |
| WO | WO 95/01179 | 1/1995 |
| WO | WO 98/11049 | 3/1998 |
| WO | WO 00/ 13685 | 3/2000 |
| WO | WO 00/54767 | 9/2000 |
| WO | WO 01/70664 | 9/2001 |

OTHER PUBLICATIONS

Merriam Webster's Collegiate Dictionary, 10th edition, Merriam-Webster, Inc.: Springfield, MA, 1993, pp. 145, 864, and 1307.*
Levy et al. "A Novel Polyisoprenyl Phosphate Signaling Cascade in Human Neutrophils" Ann. NY Acad. Sci. 2000, 905, 69-80 (abstract only).*
Merck Manual Home Edition Online articles: "Chronic Obstructive Pulmonary Disease;" "Bronchiectasis;" Acute Respiratory Distress Syndrome: "Idiopathic Pulmonary Fibrosis;" "Respiratory Tract Infections;" "Hypersensitivity Pneumonitis;" and "Sarcoidosis."*
Oh, P. I. et al. "Cocaine Induced Eosinophilic Lung Disease," Thorax, 1992, 47, 478-479.*
Wikipedia online encyclopedia entry on bronchiolitis, May 29, 2006; http://en.wikipedia.org/wiki/bronchiolitis.*
EMedicine online articles, accessed May 29, 2006, regarding Bronchiolitis Obliterans Organizing Pneumonia and Wegener Granulomatosis: http://www.emedicine.com/radio/topic117.htm and http://www.emedicine.com/RADIO/topic743.htm , respectively.*
Merck Manual Home Edition Online articles: "Bronchitis" and "Allergic Bronchopulmonary Aspergillosis", accessed Feb. 14, 2007.*
Trivedi et al. "Biomedicine & Diseases: Review," Cell. Mol. Life Sci. 2007, 64, pp. 1269-1289.*
Levy, B. D. et al. "Protectin D1 is Generated in Asthma and Dampens Airway Inflammation and Hyperresponsiveness," The Journal of Immunology, 2007, 178, pp. 496-502.*
Levy, B. D. et al. "Multi-pronged Inhibition of Airway Hyper-Responsiveness and Inflammation by Lipoxin A4," Nature Medicine, 2002, 8(9), pp. 1018-1023.*
Jacobsen, E. A. et al. "Eosinophils and Asthma," Current Allergy and Asthma Reports, 2007, 7, pp. 18-26.*
Peter J. Barnes, "Anti-Inflammatory Therapy for Asthma," Annu. Rev. Med. 1993, 44, pp. 229.*
Bosquet et al. "Eosinophilic inflammation in asthma," New England Journal of Medicine, Oct. 1990, 323, abstract.*
Barnes, P. J. "Anti-inflammatory Therapy for Asthma" Annu. Rev. Med. 1993, vol. 44, p. 229-242.*
Sanak, M. et al. "Aspirin-tolerant Asthmatics Generate More Lipoxins than Aspirin-Intolerant Asthmatics," Eur. Respir. J. 2000, 16, 44-49.*
Merriam Webster's Collegiate Dictionary, 10th Edition, Merriam-Webster, Inc.: Springfield, MA, 1993, pp. 145, 864 and 1307.
Levy et al., "A Novel Polyisoprenyl Phosphate Signaling Cascade in Human Neutrophils", Ann. NY Acad. Sci., 2000, 905, 69-80 (abstract only).
Oh, P.I. et al. "Cocaine Induced Eosinophilic Lung Disease," Thorax, 1992, 47, 478-479.

(Continued)

Primary Examiner — James H Alstrum-Acevedo
(74) Attorney, Agent, or Firm — Colin L. Fairman; Scott D. Rothenberger; Fulbright & Jaworski

(57) ABSTRACT

The use of lipoxin analogs for the treatment or prevention of asthma and asthma related diseases is described. In particular, acetylenic lipoxin analogs are effective for the treatment and prevention of eosinophil recruitment involved with the inflammation processes associated with asthma, asthma like conditions, and lung injuries associated from airway inflammation or infection as brought about by leukocyte-mediated injury from within.

1 Claim, 9 Drawing Sheets

OTHER PUBLICATIONS

Wikipedia online encyclopedia entry on bronchiolitis, May 29, 2006; en.wikipedia.org/wiki/bronchiolotis.
Emedicine online articles, accessed May 29, 2006, regarding Bronchiolitis Obliterans Organizing Pneumonia and Wegener Granulomatosis: www.emedicine.com/radio/topic117.htm and www/emedicine.com/RADIO/topic743.htm, respectively.
European Office Action for EP 02789515.0 dated Nov. 23, 2007.
European Search Report for EP 07021305 dated Mar. 20, 2008.
Shum, Daisy K.Y. et al. "Neutrophil-mediated degradation of lung proteoglycans: stimulation by tumor necrosis factor-alpha in sputum of patients with bronchiectasis", American Journal of Respiratory and Critical Care Medicine, vol. 162, No. 5, Nov. 2000, pp. 1925-1931, XP002465538.
Prasse A. et al. "Th1 cytokine pattern in sarcoidosis is expressed by bronchoalveolar CD4+ and CD8+ T cells", Clinical and Experimental Immunology, vol. 122, No. 2, Nov. 2000, pp. 241-248. XP002465539.
Webber, S.E. et al. Adv. Exp. Med. Biol. 229:61 (1988).
Reduchal, B. et al. Adv. Prostaglandin Thromboxane Leukotriene Res. 14:263 (1985).
Berge, S.M. et al. "Pharmaceutical Salts", J. Pharm. Sci., 66:1-19 (1977).
Corey, et al., "On the Synthesis and Structure of Lipoxin B", Tetrahedron Letters, vol. 26, No. 16, (1985) pp. 1919-1922.
Tankano, et al., "Neutrophil-mediated Changes in Vascular Permeability Are Inhibited by Topical Application of Aspiring-triggered 15-epi-lipoxin A4 and Novel Lipoxin B4", J. Clin. Invest. The American Society for Clinical Investigations, Inc., vol. 101, No. 4, 1998, pp. 819-826.
Nguyen, et al. "Nonsteroidal anti-inflammatory drug use in dentistry: Gastrointestinal Implications", Pharmacology, Nov. 1999, pp. 590-596.
Maddox, et al., "Lipoxin B4 Regulates Human Monocyte/Neutrophil Adherence and Motility: Design of Stable Lipoxin B4 Analogs with Increased Biologic Activity", The FASEB Journal, vol. 12, Apr. 1998, pp. 487-494.
Poullot, et al, "Lipoxin A4 and Aspirin-Triggered 15-EPI-LXA4 Inhibit Tumor Necrosisfactor-Alpha-Initiated Neutrophil Responses and Trafficking: Novel Regulators of a Cytokine-Chemokine Axis Relevant to Periodontal Diseases", Journal of Periodontal Research, vol. 34, No. 7, Oct. 1999, pp. 370-373.
Fiore et al., "Lipoxin Recognition Sites", The Journal of Biological Chemistry, vol. 267, No. 23. 1992, pp. 16168-16176.
Claria, J. et al., Aspirin Triggers Previously Undescribed Bioactive Eicosanoids by Human Endothelial Cell-Leukocyte Interactions:, Proc, Nat'l Acad. Sci, vol. 92, 1995, pp. 9475-9479.
Serhan, "Lipoxins: Eicosanoids Carrying Intra- and Intercellular Messages", Journal of Bioenergetics and Biomembranes, vol. 23, No. 1, 1991, pp. 105-122.
Mizukami, et al., "ω-Hydroxylation of Lipoxin $B_4$ by Human Neutrophil Microsomes: Identification of ω-Hydroxy Metabolite of Lipoxin $B_4$ and Catalysis by Leukotriene $B_4$ ω-Hydroxylase (cytochrome P-450LTBω)", Biochimica et Biophysica Acta, No. 1168, 1993, pp. 87-93.
Popov, et al., "Effect of Lipoxin B on Colony-Forming Ability of Human Peripheral Blood Mononuclears in a Diffusion Chamber", Translated from Byulleten' Eksperimental' noi Biologii i Meditsiny, vol. 107, No. 1, 1989, pp. 80-83.
Katoh, et al., "Renal Hemodynamic Actions of Lipoxin in Rats: A Comparative Physiological Study", American Journal Physiology, vol. 263, 1992, pp. F436-F442.
Nigam, et al., "Lipoxin $A_4$ and Lipoxin $B_4$ Stimulate the Release but not the Oxygenation of Arachidonic Acid in Human Neutrophils: Dissociation between Lipid Remodeling and Adhesion", Journal of Cellular Physiology, Vo. 142, 1990, pp. 512-523.
Lee, et al., "Inhibition of Leukotriene $B_4$ —Induced Neutrophil Migration by Lipoxin $A_4$: Structure-Function Relationships", Biochemical and Biophysical Research Communications, vol. 180, No. 3, 1991, pp. 1416-1421.
Nicolaou, et al., "Lipoxins and Related Eicosanoids: Biosynthesis, Biological Properties, and Chemical Synthesis", Angew. Chem. Int. Ed. Engl., vol. 30, 1991, pp. 1100-1116.

Nicolaou, et al., "Total Synthesis of Novel Geometric Isomers of Lipoxin $A_4$ and Lipoxin $B_4$", Reprint from The Journal of Organic Chemistry, vol. 54, No. 23, 1989, pp. 5527-5535.
Brady, et al., "Leukotrienes Stimulate Neutrophil Adhesion to Mesangial Cells: Modulation with Lipoxins", American Journal Physiology, vol. 259, 1990, pp. F809-F815.
Nicolaou et al., "Identification of a novel 7-cis-11-trans-lipoxin $A_4$ generated by human neutrophils: total synthesis, spasmogenic activities and comparison with other geometric isomers of lipoxins $A_4$ and $B_4$", Biochimica et Biophsica Acta, 1003, 1989, pp. 44-53.
Serhan et al., "Design of Lipoxin A4 Stable Analogs That Block Transmigration and Adhesion of Human Neutrophils", Biochemistry, vol. 34, No. 44, 1995, pp. 14609-14615.
Maddox, et al., "Lipoxin A4 Stable Analogs Are Potent Mimetics That Stimulate Human Monocytes and THP-1 Cells via a G-protein-linked Lipoxin A4 Receptor", The Journal of Biological Chemistry, vol. 272, No. 11, 1997, pp. 6972-6978.
Claria, J. "Aspirin-Triggered Lipoxins (15-epi-LX) Are Generated by the Human Lung Adenocarcinoma Cell Line (A549)—Neutrophil Interactions and Are Potent Inhibitors of Cell Proliferation", Molecular Medicine, vol. 2, No. 5, Sep. 1996, pp. 583-596.
Badr, K.F. "15-Lipoxygenase Products as Leukotriene Antagonists: Therapeutic Potential in Glomerulonephritis", Kidney International, vol. 42, Supp. 38, 1992, pp. S101-S108.
Fiore, S. "The Lipoxin Biosynthetic Circuit and their Actions with Human Neutrophils", Advances in Experimental Medicine and Biology, vol. 314, 1991, pp. 109-132.
Fiore, S, et al. "Induction of Functional Lipoxin A4 Receptors in HL-60 Cells", Blood, vol. 81, No. 12, 1993, pp. 3395-3403.
Lederman, S. et al. "Identification of a Novel Surface Protein on Activated CD4+ T Cells that Induces Contact-Dependent B Cell Differentiation (Help)", J. Exp. Med., vol. 175, 1992, pp. 1091-1101.
Madara, J.L. et al. "A Simple Approach to Measurement of Electrical Parameters of Cultured Epithelial Monolayers: Use in Assessing Neutrophil-Epithelial Interactions", J. Tiss. Cult. Meth., vol. 14, 1992, pp. 209-216.
Madara, J.L. et al. "5'-Adenosine Monophosphate is the Neutrophil-derived Paracrine Factor that Elicits Chloride Secretion from T84 Intestinal Epithelial Cell Monolayers", J. Clin. Invest., vol. 91, 1993, pp. 2320-2325.
Nash, S. et al. "Effects of Polymorphonuclear Leukocyte Transmigration on the Barrier Function of Cultured Intestinal Epithelial Monolayers", J. Clin. Invest., vol. 80, 1987, pp. 1104-1113.
Noelle, R.J. et al., "A 39-kDa Protein on Activated Helper T Cells Binds CD40 and Transduces the Signal for Cognate Activation of B Cells", Proc. Natl. Acad. Sci. USA, vol. 89, 1992, pp. 6550-6554.
Parkos, C.A. et al. "Neutrophil Migration Across a Cultured Intestinal Epithelium", J. Clin. Invest., vol. 88, 1991, pp. 1605-1612.
Parkos, C.A. et al. "Neutrophil Migration Across a Cultured Epithelial Monolayer Elicits a Biphasic Resistance Response Representing Sequential Effects on Transcellular and Paracellular Pathways", The Journal of Cell Biology, vol. 117, No. 4, 1992, pp. 757-764.
Pettitt, T.R. et al., "Synthesis of Lipoxins and Other Lipoxygenase Products by Macrophages form the Rainbow Trout, Oncorhynchus Mykiss", The Journal of Biological Chemistry, vol. 266, No. 14, 1991, pp. 8720-8726.
Samuelsson, B., "An Elucidation of the Arachidonic Acid Cascade Discovery of prostaglandins, Thromboxane and Leukotrienes", Drugs, vol. 33, Supp. 1, 1987, pp. 209.
Leff, A.R. "Role of Leukotrienes in Bronchial Hyperresponsiveness and Cellular Responses in Airways", Amer. Journal of Respiratory and Critical Care Medicine, vol. 161, 2000, pp. S125-S132.
Bousquet, J. et al. "Asthma. From bronchoconstriction to Airways Inflammation and Remodeling", Amer. Journal of Respiratory and Critical Care Medicine, vol. 161, 2000, pp. 1720-1745.
Robinson, D.S. et al. "Predominant TH2-like Bronchoalveolar T-lymphocyte Population in Atopic Asthma", New England Journal of Medicine, vol. 326, 1992, pp. 298-304.
Broide, D.H. et al. "Cytokines in Symptomatic Asthma Airways", J. Allergy Clin. Immunol., vol. 89, 1992, pp. 958-967.

Samuelsson, B. "From Studies of Biochemical Mechanisms to Novel Biological Mediators: Prostaglandin Endoperoxides, Thromboxanes and Leukotrienes", *In Les Prix Nobel: Nobel Prizes, Presentations, Biographies and Lectures*, 1982, pp. 153-174.

Drazen, J.M. et al. "Treatment of Asthma with Drugs Modifying the Leukotriene Pathway", *New England Journal of Medicine*, vol. 340, 1999, pp. 197-206.

Serhan, C.N. et al. "Lipid Mediator Networks in Cell Signaling: Update and Impact of Cytokines", *FASEB Journal*, vol. 10, 1996, pp. 1147-1158.

McMahon, B. et al. "Lipoxins: Revelations on Resolution", *Trends in Pharmacological Sciences*, vol. 22, 2001, pp. 391-395.

Levy, B.D. et al. "Lipid Mediator Class Switching During Acute Inflammation: Signals in Resolution", *Nature Immunology*, vol. 2, 2001, pp. 612-619.

Lee, T.H. et al. "Identification of Lipoxin A4 and its Relationship to Sulfidopeptide Leukotrienes C4, D4, and E4 in the Bronchoalveolar Lavage Fluids obtained from patients with Selected Pulmonary Diseases", *Amer. Review of Respiratory Disease*, vol. 141, 1990, pp. 1453-1458.

Badr, K.F. et al., "Lipoxin A4 Antagonizes Cellular and in Vivo Actions of Leukotriene D4 in rat glomerular mesangial cells: Evidence for Competition at a Common Receptor", *Proc. Nat'l. Acad. Sci. USA*, vol. 86, 1989, pp. 3438-3442.

Gronert K. et al. "Selectivity of Recombinant Human Leukotriene D4 Leukotriene B4 and Lipoxin A4 Receptors with Aspirin-Triggered 15-epi-LXA4 and Regulation of Vascular and Inflammatory Responses", *Amer. J. Path*, vol. 158, 2001, pp. 3-9.

Takano, T. et al. "Aspirin-Triggered 15-epi-lipoxin A4 (LXA4) and LXA4 Stable Analogues are Potent Inhibitor of Acute Inflammation: Evidence for Anti-Inflammatory Receptors", *Journal of Experimental Medicine*, vol. 185, 1997, pp. 1693-1704.

De Sanctis, G.T. et al. "Interleukin-8 Receptor Modulates IgE Production and B-cell Expansion and Trafficking in Allergen-Induced Pulmonary Inflammation", *J. Clin. Invest.*, vol. 103, 1999, pp. 507-515.

De Sanctis, G.T. et al. "Contribution of Nitric Oxide Synthases 1, 2, and 3 to Airway Hyperresponsiveness and Inflammation in a Murine Model of Asthma", *Journal of Experimental Medicine*, vol. 189, 1999, pp. 1621-1630.

Clish, C.B. et al. "Local and Systemic Delivery of a Stable Aspirin-Triggered Lipoxin Prevents Neutrophil Recruitment in Vivo", *Proc. Nat'l. Acad. Sci. USA*, vol. 96, 1999, pp. 8247-8452.

Holgate, S.T. "The Epidemic of Allergy and Asthma", *Nature*, vol. 402, 1999, pp. B2-B4.

Drazen, J.M. et al. "Heterogeneity of Therapeutic Responses in Asthma", *British Medical Bulletin*, vol. 56, 2000, pp. 1054-1070.

Bryan, S.A. et al. "Effects of Recombinant Human Interleukin-12 on Eosinophils, Airway Hyper-Responsiveness, and the late Asthmatic Response", *Lancet*, vol. 356, 2000, pp. 2149-2153.

Leckie, M.J. et al. "Effects of an Interleukin-5 Blocking Monoclonal Antibody on Eosinophils, Airway Hyper-Responsiveness, and the lat Asthmatic Response", *Lancet*, vol. 356, 2000, pp. 2144-2148.

Christie, P.E. et al. "The Effects of Lipoxin A4 on Airway Responses in Asthmatic Subjects", *Amer. Review of Respiratory Disease*, vol. 145, 1992, pp. 1281-1284.

Dahlen, S.E. et al. "Actions of Lipoxin A4 and Related Compounds in Smooth Muscle Preparations and on the Microcirculation in vivo", *Advances in Experimental Medicine & Biology*, vol. 229, 1988, pp. 107-130.

Venkayya, R. et al. "The Th2 Lymphocyte Products IL-4 and IL-13 Rapidly Induce Airway Hyperresponsiveness Through Direct Effects on Resident Airway Cells", *Amer. Journal of Respiratory Cell & Molecular Biology*, vol. 26, 2002, pp. 202-208.

Laporte, J.C. et al. "Direct Effects of Interleukin-13 on Signaling Pathways for Physiological Responses in Cultured Human Airway Smooth Muscle Cells", *Amer. Journal of Respiratory & Critical Care Medicine*, vol. 164, 2001, pp. 141-148.

Cowburn, A.S. et al. "IL-5 Increases Expression of 5-Lipoxygenase-activating Protein and Translocates 5-Lipoxygenase to the Nucleus in Human Blood Eosinophils", *J. Immun.*, vol. 163, 1999, pp. 456-465.

Hisada, T. et al. "Cysteinyl-leukotrienes Partly Mediate Eotaxin-Induced Bronchial Hyperresponsiveness and Eosinophilia in IL-5 Transgenic Mice", *Amer. Journal of Respiratory & Critical Care Medicine*, vol. 160, 1999, pp. 571-575.

Drazen, J.M. "Leukotrienes as Mediators of Airway Obstruction", *Amer. Journal of Respiratory & Critical Care Medicine*, vol. 158, 1998, pp. S193-S200.

Resnati, M. et al. "The Fibrinolytic Receptor for Urokinase Activates the G-protein-coupled Chemotactic Receptor FPRL1/LXA4R", *Proc. Nat'l. Acad. Sci.*, vol. 99, 2002, pp. 1359-1364.

Soyombo, O. et al. "Effects of Lipoxin A4 on Chemotaxis and Degranulation of Human Eosinophils Stimulated by Platelet- Activating Factor and N-formly-L-methionyl-L-leucyl-L-phenylalanine", *Allergy*, vol. 49, 1994, pp. 230-234.

Bandeira-Melo, C. et al. "Cutting Edge: Lipoxin (LX) A4 and Aspirin-Triggered 15-epi-LXA4 Block Allergen-Induced Eosinophil Trafficking", *J. Immun.*, vol. 164, 2000, pp. 2267-2271.

Bandeira-Melo, C. et al. "Cyclooxygenase-2-dervied Prostaglandin E2 and Lipoxin A4 Accelerate Resolution of Allergic Edema in Angiostrongylus Costaricensis-infected Rats: Relationship with Concurrent Eosinophilia", *J. Immun.*, vol. 164, 2000, pp. 1029-1036.

Aliberti, J. et al. "Lipoxin-Mediated Inhibition of IL-12 Production by DCs: A Mechanisn for Regulation of Microbial Immunity", *Nature Immunology*, vol. 3, 2002, pp. 76-82.

Sanak, M. et al. "Aspirin-tolerant Asthmatics Generate More Lipoxins than Aspirin-intolerant Asthmatics", *European Respiratory Journal*, vol. 16, 2000, pp. 44-49.

Chiang N. et al. "Leukotriene B4 Receptor Transgenic Mice Reveal Novel Protective Roles for Lipoxins and Aspirin-Triggered Lipoxins in Reperfusion", *J. Clin. Invest.*, vol. 164, 1999, pp. 309-316.

Wu, W. et al. "Eosinophils Generate Brominating Oxidants in Allergen-induced Asthma", *J. Clin. Invest.*, vol. 105, 2000, pp. 1455-1463.

International Search Report.

* cited by examiner

METHOD FOR TREATING AIRWAY HYPER-RESPONSIVENESS WITH LIPOXIN ANALOGS

RELATED APPLICATIONS

This application is a divisional of and claims priority to U.S. application Ser. No. 10/289,654, filed Nov. 6, 2002, which claims benefit of U.S. Provisional Application No. 60/338,862, filed Nov. 6, 2001, entitled "Lipoxins and Aspirin-Triggered Lipoxins and Their Stable Analogs in the Treatment of Asthma and Inflammatory Airway Diseases" and U.S. Provisional Application No. 60/391,049, filed on Jun. 24, 2002, entitled "Lipoxins and Aspirin-Triggered Lipoxins and Their Stable Analogs in the Treatment of Asthma and Inflammatory Airway Diseases" the contents of which are incorporated herein by reference.

STATEMENT REGARDING FEDERALLY SPONSORED RESEARCH

The work leading to this invention was supported in part by National Institutes of Health (NIH) grants GM-38765, P01-DE13499 and K08 HL03788. The U.S. Government therefore may have certain rights in the invention.

BACKGROUND

Asthma is characterized by airway hyper-responsiveness and chronic airway inflammation[1]. Large numbers of eosinophils and T lymphocytes infiltrate peribronchial tissues in asthmatics[2], trafficking into the lung an increased capacity to generate cysteinyl leukotrienes (CysLT's) and $T_H2$ cytokines[1,3,4]. CysLT's have been associated with the asthmatic diathesis in both experimental models and patients with asthma[5,6]. One of the many actions of $T_H2$ cytokines is to up-regulate the expression of biosynthetic enzymes for eicosanoids—including leukotrienes and lipoxins (LX's)[7,8].

LX's are a separate class of eicosanoids that are distinct in structure and function[7], and their biosynthesis is temporally dissociated from the formation and impact of other eicosanoids[9]. LX's are generated in human tissues, including airways[10]. LX's carry unique counter-regulatory actions that inhibit CysLT-mediated vascular responses[11] and promote resolution of cytokine-driven acute inflammation[9]. When administered to human cells in vitro or murine systems in vivo, at least two classes of receptors, CysLT1 receptors and $LXA_4$ receptors (designated ALX), can interact with LX's to mediate their actions[12,13]. A role for LX's in asthma has not yet been directly evaluated in well-qualified experimental animal models.

The global prevalence of asthma continues to increase, affecting millions of peoples' daily lives, but treatment is far from ideal[18]. Clinical responses to current therapies, such as inhaled corticosteroids and leukotriene modifiers are heterogeneous[19] and even with optimal treatment there is a substantial burden of unaddressed disease.

With further evidence for serious toxicity from exogenous corticosteroids, new anti-inflammatory strategies are needed for asthma and other allergic illnesses.

SUMMARY

It has been surprisingly discovered that lipoxins (LX's) of the invention, discussed infra, decrease both airway inflammation and hyper-responsiveness in response to allergen sensitization and aerosol challenge. Consequently, the lipoxins disclosed herein are useful for the treatment and/or prevention of asthma and related airway and respiratory inflammatory disorders.

The present invention pertains to methods for treating or preventing conditions associated with asthma, a related airway or respiratory inflammatory disorder. The methods include administration to a subject, an effective amount of a lipoxin analog, having the formula described infra, such that the asthma or related airway or respiratory inflammatory disorder is treated.

Exemplary compounds useful in the treatment of the above-identified ailments include:

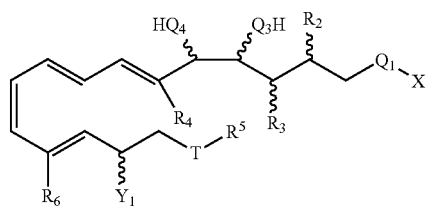

Formula (I)

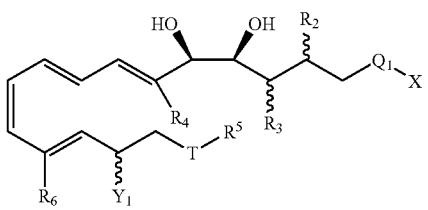

Formula (II)

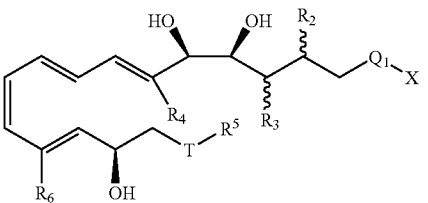

Formula (III)

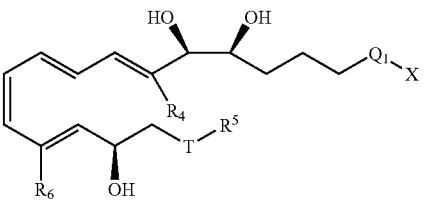

Formula (IV)

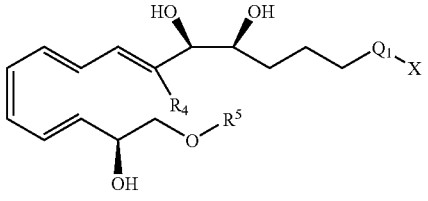

Formula (V)

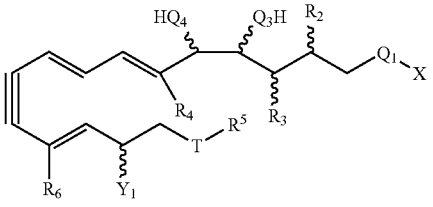

Formula (VI)

-continued

Formula (VII)
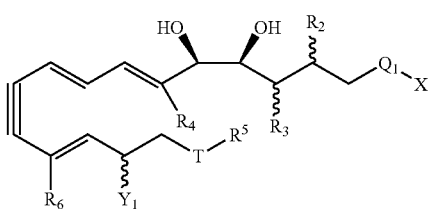

Formula (VIII)
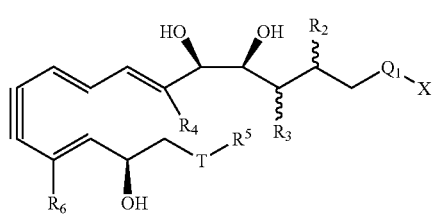

Formula (IX)
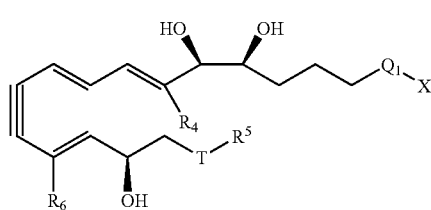

Formula (X)
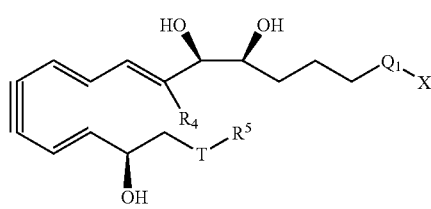

Formula (XI)
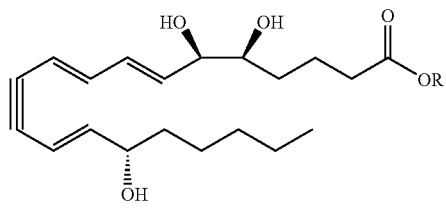

wherein X, if present, is $R_1$, $OR_1$, or $SR_1$;
wherein $R_1$, if present, is
(i) a hydrogen atom;
(ii) an alkyl of 1 to 8 carbon atoms, inclusive, which may be straight chain or branched;
(iii) a cycloalkyl of 3 to 10 carbon atoms;
(iv) an aralkyl of 7 to 12 carbon atoms;
(v) phenyl;
(vi) substituted phenyl

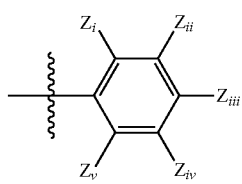

wherein $Z_i$, $Z_{ii}$, $Z_{iii}$, $Z_{iv}$ and $Z_v$ are each independently selected from $-NO_2$, $-CN$, $-C(=O)-R_1$, $-SO_3H$, a hydrogen atom, halogen, methyl, $-OR_x$, wherein $R_x$ is 1 to 8 carbon atoms, inclusive, which may be a straight chain or branched, and hydroxyl;
(vii) a detectable label molecule; or
(viii) a straight or branched chain alkenyl of 2 to 8 carbon atoms, inclusive;
wherein $Q_1$, if present, is (C=O), $SO_2$ or (CN), provided when $Q_1$ is CN, then X is absent;
wherein $Q_3$, if present, and $Q_4$, if present, are each independently O, S or NH;
wherein one of $R_2$, if present, and $R_3$, if present, is a hydrogen atom and the other is
(a) H;
(b) an alkyl of 1 to 8 carbon atoms, inclusive, which may be a straight chain or branched;
(c) a cycloalkyl of 3 to 6 carbon atoms, inclusive;
(d) an alkenyl of 2 to 8 carbon atoms, inclusive, which may be straight chain or branched; or
(e) $R_a Q_2 R_b$ wherein $Q_2$ is $-O-$ or $-S-$; wherein $R_a$ is alkylene of 0 to 6 carbon atoms, inclusive, which may be straight chain or branched and wherein $R_b$ is alkyl of 0 to 8 carbon atoms, inclusive, which may be straight chain or branched, provided when $R_b$ is 0, then $R_b$ is a hydrogen atom;
wherein $R_4$, if present, is
(a) H;
(b) an alkyl of 1 to 6 carbon atoms, inclusive, which may be a straight chain or branched;
wherein $R_5$, if present, is

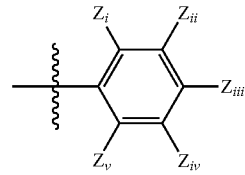

wherein $Z_i$, $Z_{ii}$, $Z_{iii}$, $Z_{iv}$ and $Z_v$ are each independently selected from $-NO_2$, $-CN$, $-C(=O)-R_1$, $-SO_3H$, a hydrogen atom, halogen, methyl, $-OR_x$, wherein $R_x$ is 1 to 8 carbon atoms, inclusive, which may be a straight chain or branched, and hydroxyl or a substituted or unsubstituted, branched or unbranched alkyl group;
wherein $Y_1$, if present, is $-OH$, methyl, $-SH$, an alkyl of 2 to 4 carbon atoms, inclusive, straight chain or branched, an alkoxy of 1 to 4 carbon atoms, inclusive, or $CH_a Z_b$ where a+b=3, a=0 to 3, b=0 to 3 and Z is cyano, nitro or a halogen;
wherein $R_6$, if present, is
(a) H;
(b) an alkyl from 1 to 4 carbon atoms, inclusive, straight chain or branched;
wherein T, if present, is O or S, and pharmaceutically acceptable salts thereof.

In certain embodiments, the methods of the invention are performed in vitro or in vivo.

In another aspect, the present invention is directed to a packaged pharmaceutical composition for treating the activity or conditions described herein in a subject. The packaged pharmaceutical composition includes a container holding a therapeutically effective amount of at least one lipoxin compound having one of the formulae described infra and instructions for using the lipoxin compound for treating the activity or condition in the subject.

BRIEF DESCRIPTION OF THE DRAWINGS

The invention will be more fully understood from the following detailed description taken in conjunction with the accompanying drawings, in which.

DETAILED DESCRIPTION

Figure 1:
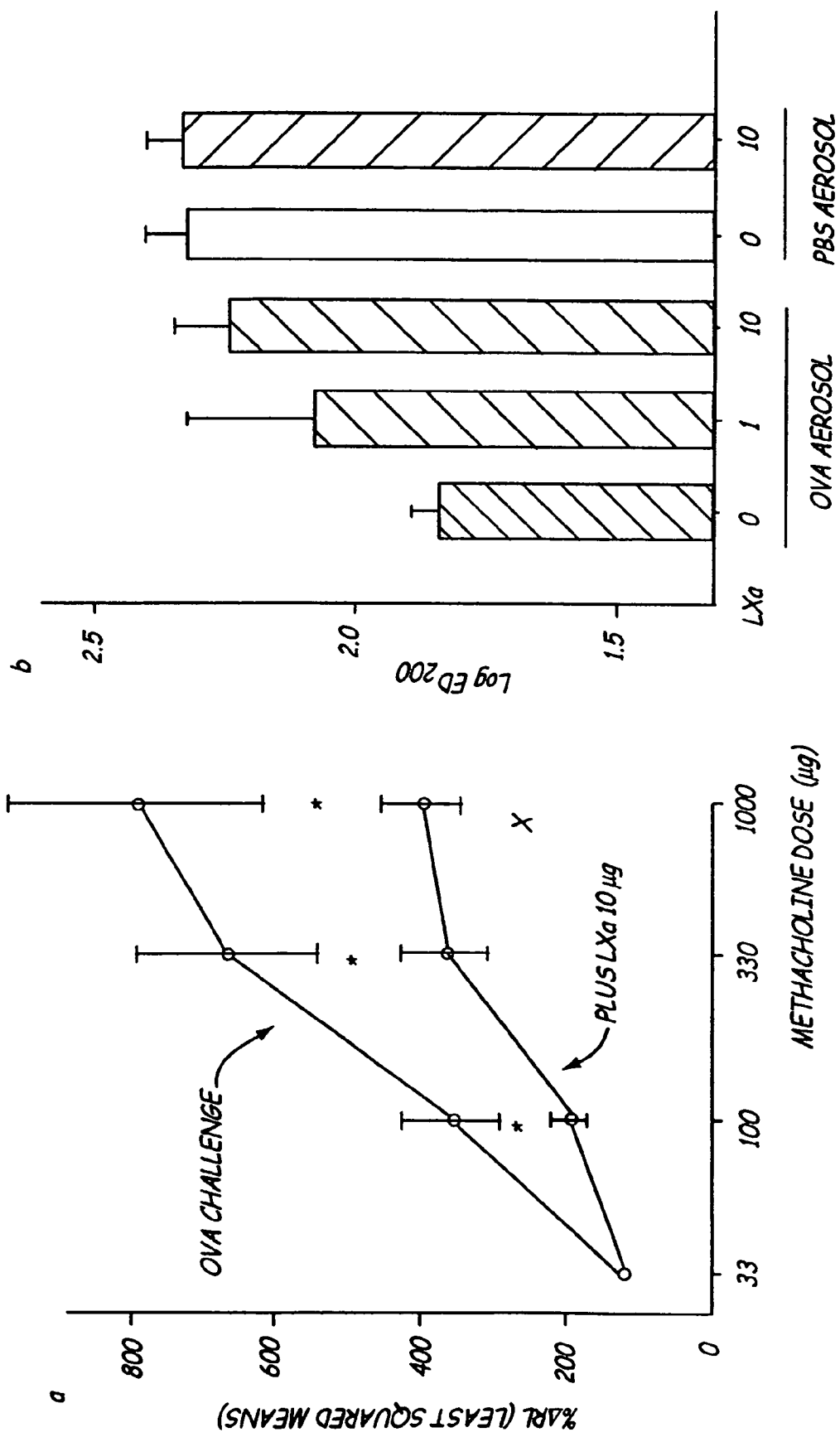
FIG. 1. Inhibition of airway hyper-responsiveness with LXa. OVA sensitized mice were treated with LXa (μg) (o) or vehicle (•) prior to OVA aerosol challenge. Airway reactivity was determined by methacholine-dependent change in lung resistance (a) and calculation of $ED_{200}$ (b). Results are expressed as mean±SEM (n≧17 in (a) and n≧6 (b)). *P<0.05 by Student's t-test compared to control animals.

The features and other details of the invention will now be more particularly described and pointed out in the claims. It will be understood that the particular embodiments of the invention are shown by way of illustration and not as limitations of the invention. The principle features of this invention can be employed in various embodiments without departing from the scope of the invention.

The prevalence of asthma continues to increase and its optimal treatment remains a challenge. The present invention pertains to methods that involve the actions of lipoxin $A_4$ and its leukocyte receptor in pulmonary inflammation using a murine model of asthma. Allergen challenge initiated airway biosynthesis of lipoxin $A_4$ and increased expression of its receptor. Administration of a stable analogs of lipoxin $A_4$ blocked both airway hyper-responsiveness and pulmonary inflammation, as evidenced by decreased recruitment of leukocytes as well as reduced mediator levels, including interleukin-5, interleukin-13, eotaxin, prostanoids and cysteinyl leukotrienes. Moreover, transgenic expression of human lipoxin $A_4$ receptors in murine leukocytes led to significant inhibition of both pulmonary inflammation and eicosanoid-initiated eosinophil tissue infiltration. Inhibition of airway hyper-responsiveness and allergic airway inflammation with a lipoxin $A_4$ stable analogs highlights a unique counter-regulatory profile for the lipoxin $A_4$ system and its leukocyte receptor in airway responses and suggest that lipoxin and related pathways present novel multi-pronged therapeutic approaches for consideration in human asthma.

Lipoxin $A_4$ ($LXA_4$) is rapidly generated from arachidonic acid during inflammatory responses, and, unlike leukotrienes (LT), $LXA_4$ and its stable analogs carry anti-inflammatory properties that promote resolution of acute exudative inflammation. The present invention demonstrates that $LXA_4$ also regulates airway inflammation and bronchial reactivity, characteristic features of asthma. High levels of both cysteinyl LT and prostaglandin $E_2$ ($PGE_2$) in bronchoalveolar lavage (BAL) fluids from ovalbumin (OVA) sensitized and aerosol were found in challenged mice. $LXA_4$ was also identified in these same samples, yet in concentrations 1-2 log orders less (15.01+/−3.26 pg/ml, mean+/−SEM, n=5) than LT and PG, respectively. When an $LXA_4$ stable analog (including its 11, 12 acetylenic version) was given 1-2 h prior to OVA aerosol challenge, a marked reduction in tissue eosinophils, neutrophils, lymphocytes and vascular injury was observed. The LX analogs also led to decreased concentrations of IL-5, IL-13 and eotaxin, but not IL-12 or TNF in OVA sensitized and challenged animals. Lipid mediator formation was also selectively down-regulated by LX analog administration as levels of $PGE_2$ and cysteinyl LT's, but not $LTB_4$ were decreased. In addition to inflammatory responses, administration of the LX analog significantly inhibited bronchoconstriction in response to methacholine with an ED200 that approximated that of unchallenged mice. Because $LXA_4$ can interact with cysLT1 receptors, it was determined that LX administration alone would promote airway hyperreactivity in vivo, and no significant differences were present in ED200 compared to control mice. Since $LXA_4$ displayed potent inhibition of eosinophil tissue infiltration, it was next determined the impact of over-expression of its receptors (ALXR) on agonist-initiated eosinophil accumulation. Thirteen hours after application of $LTB_4$ and $PGE_2$ to mouse ear skin, punch biopsies were obtained for histology and quantitation of eosinophil peroxidase activity. Compared to littermate control animals, increased expression of ALXR profoundly inhibited eosinophil infiltration in two separate transgenic lines. Together, these findings indicate that both increased $LXA_4$ bioavailability via utilization of a stable analog and increased ALXR expression can mediate potent inhibition of airway inflammation and eosinophil responses in vivo. Hence, this invention reports a novel use for lipoxins, aspirin-triggered lipoxins and their structural analogs in airway inflammation, asthma and related disorders.

Eicosanoid Formation During Antigen-Initiated Airway Inflammation.

After systemic sensitization to ovalbumin (OVA, 10 µg i.p.), male Balb/c mice (5-7 weeks) were exposed to aerosolized OVA (6%, 25 min) on four successive days. 24 hours after the last aerosol, bronchial responsiveness to intravenous methacholine was determined (as in refs. 14, 15), bronchoalveolar lavage was performed and tissues were harvested for microscopy. Animals so treated demonstrate both airway hyper-responsiveness to methacholine and inflammation (vide infra), including leukocytic infiltration and elaboration of cytokines, chemokines and bioactive lipids. After allergen sensitization and aerosol challenge, high levels of both CysLT (139.0+/−27.3 pg CysLT/ml, mean+/−SEM, n=9) and $PGE_2$ (1117.7+/−103.8 pg $PGE_2$/ml, mean+/−SEM, n=5) in bronchoalveolar lavage (BAL) (Table 1) were identified. In these same BAL fluids, $LXA_4$ was also present (15.0+/−3.3 pg $LXA_4$/ml, mean+/−SEM, n=5) at levels similar to $LTB_4$ (6.4+/−2.3 pg $LTB_4$/ml, mean+/−SEM, n=9), but in 10- to 100-fold lower concentrations than CysLT's and $PGE_2$, respectively (Table 1). $LXA_4$ was not detected in cell-free BAL supernatants from non-immunized mice.

Lipoxin $A_4$ Prevents Airway Hyper-Responsiveness to Methacholine.

To determine if $LXA_4$ would protect mice from OVA-induced airway hyper-responsiveness, 10 µg/mouse (i.v.) of a $LXA_4$ analog (LXa) was administered that resists metabolic inactivation and blocks neutrophil accumulation and exudate formation in murine dorsal air pouches[7, 16]. When given at least 60 min prior to OVA challenge, LXa significantly inhibited bronchoconstriction in response to methacholine in a dose-dependent manner (FIGS. 1a & b). The $ED_{200}$ to methacholine for mice given LXa (10 µg) approximated the responses of control mice that had been sensitized but not challenged with OVA (FIG. 1b). Neither deleterious physiologic nor behavioral effects were evident in LXa treated mice. It was also determined that LXa administration alone would promote airway hyper-reactivity in vivo, and no significant differences in ED200 compared to control mice (FIG. 1b) were found.

Lipoxin $A_4$ Inhibits Key Parameters of Allergic Pulmonary Inflammation.

Figure 2:
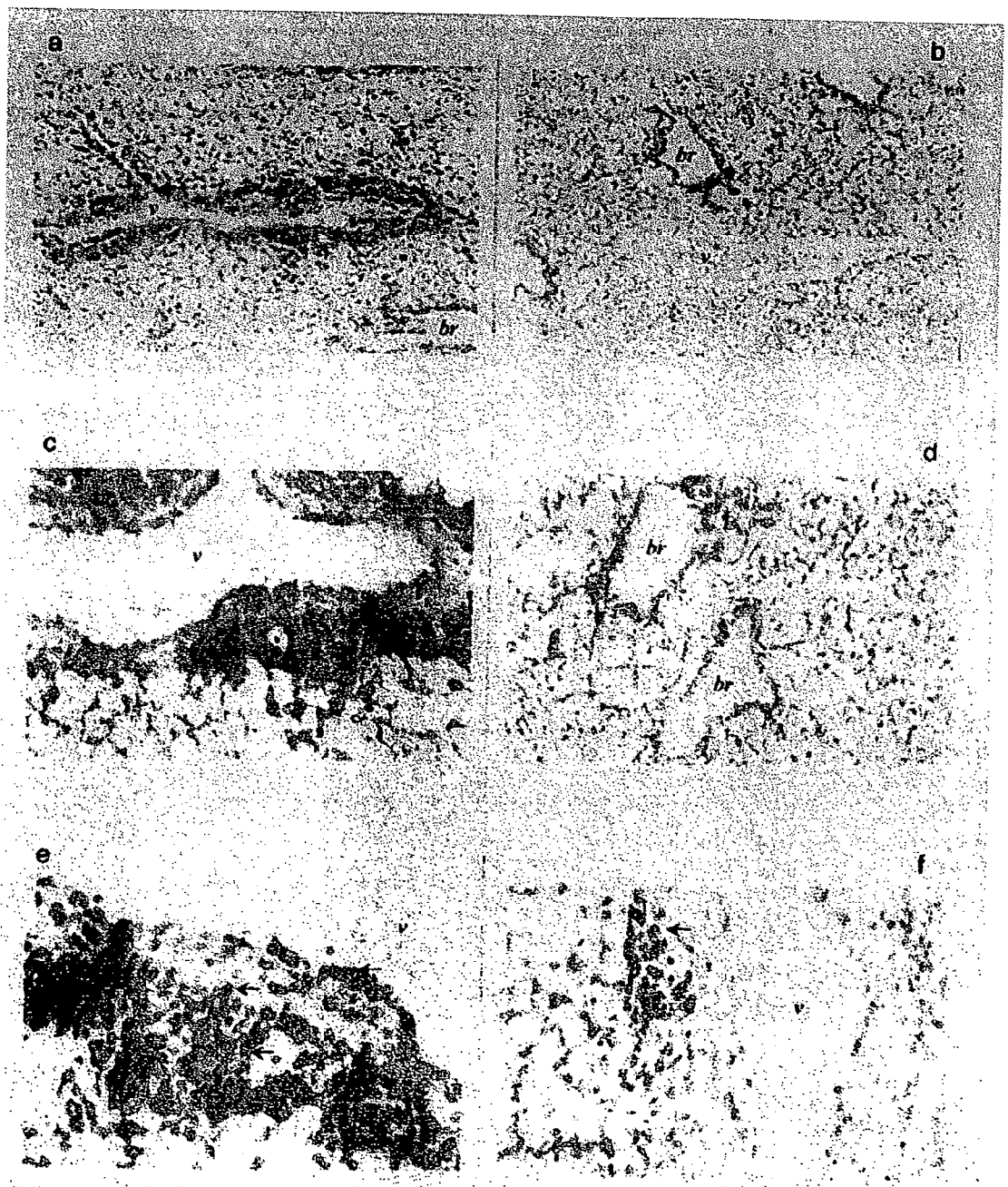
FIG. 2. Lung histopathology from LXa treated mice. Mice were sensitized and aerosol challenged with OVA in the absence (left column) or presence (right column) of LXa (10 μg). Representative (n=3) lung tissue sections (magnifications: ×40 (a,b), ×100 (d), ×200 (c,e) and ×400 (f)) were obtained from formalin-fixed, paraffin-embedded lung tissue, prepared and stained with hematoxylin and eosin. Arrows denote eosinophils; br, bronchus; v, vessel.
Figure 3:
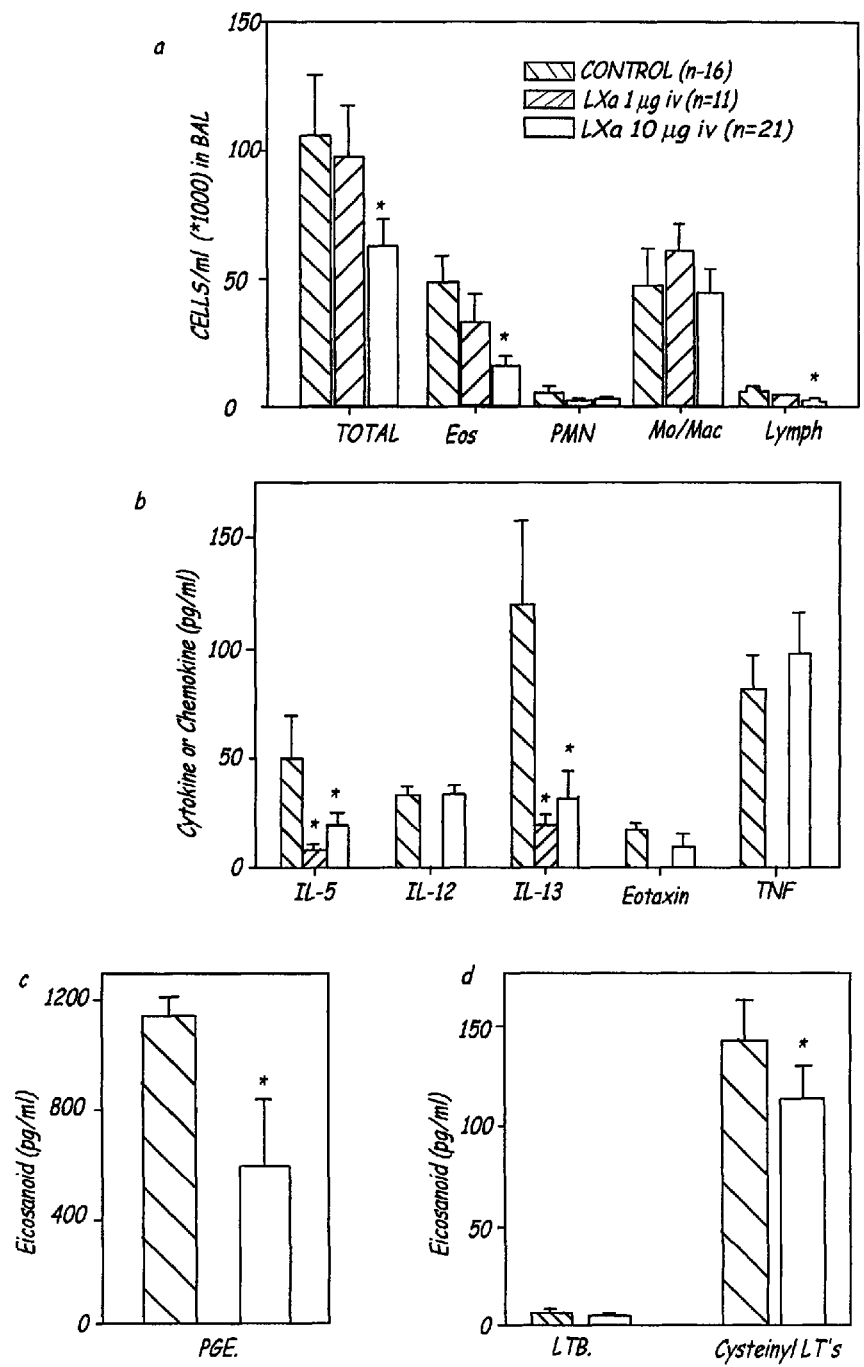
FIG. 3. LXa selectively inhibits airway leukocyte infiltration and inflammatory mediators. Bronchoalveolar lavage fluids were obtained from OVA sensitized and challenged mice. Leukocytes in bronchoalveolar lavage fluid were enumerated and identified after Wright-Giemsa stain (a). Mediator profile of (b) specific cytokines (IL-5, IL-12, IL-13, eotaxin and TNFα), and lipid mediators, including $PGE_2$ (c), $LTB_4$ and cysLT's (d) were determined by ELISA's in materials from control animals and those receiving LXa (10 μg, i.v.). Results are expressed as mean±SEM (n≧6, d≧2). *P<0.05 by Student's t-test compared to control animals.

In addition to dampening airway hyper-responsiveness in OVA-allergic mice, administration of LXa significantly reduced leukocyte infiltration, in particular, tissue eosinophils and lymphocytes as well as vascular injury (FIG. 2). In BAL, total leukocytes, eosinophils and lymphocytes were sharply reduced in a dose-dependent fashion (FIG. 3a). LXa also led to decreased $T_H2$ cytokines IL-5, IL-13 as well as eotaxin in BAL fluids from OVA sensitized and challenged animals (FIG. 3b). Inhibition appeared selective, since levels of IL-12 and TNF were not similarly reduced when determined in the same samples of BAL fluid (FIG. 3b). LXa also regulated levels of the lipid mediators, as both $PGE_2$ and CysLT's, but not $LTB_4$ were decreased in these mice (FIGS. 3c & d). These results indicate that administration of $LXA_4$ mimetics can significantly inhibit the generation of allergic pulmonary inflammation, including leukocyte infiltration and formation of specific mediators of interest in airway pathophysiology, including key cytokines and eicosanoids.

Expression of Human $LXA_4$ Receptors Dampens Pulmonary Inflammation.

Figure 4:
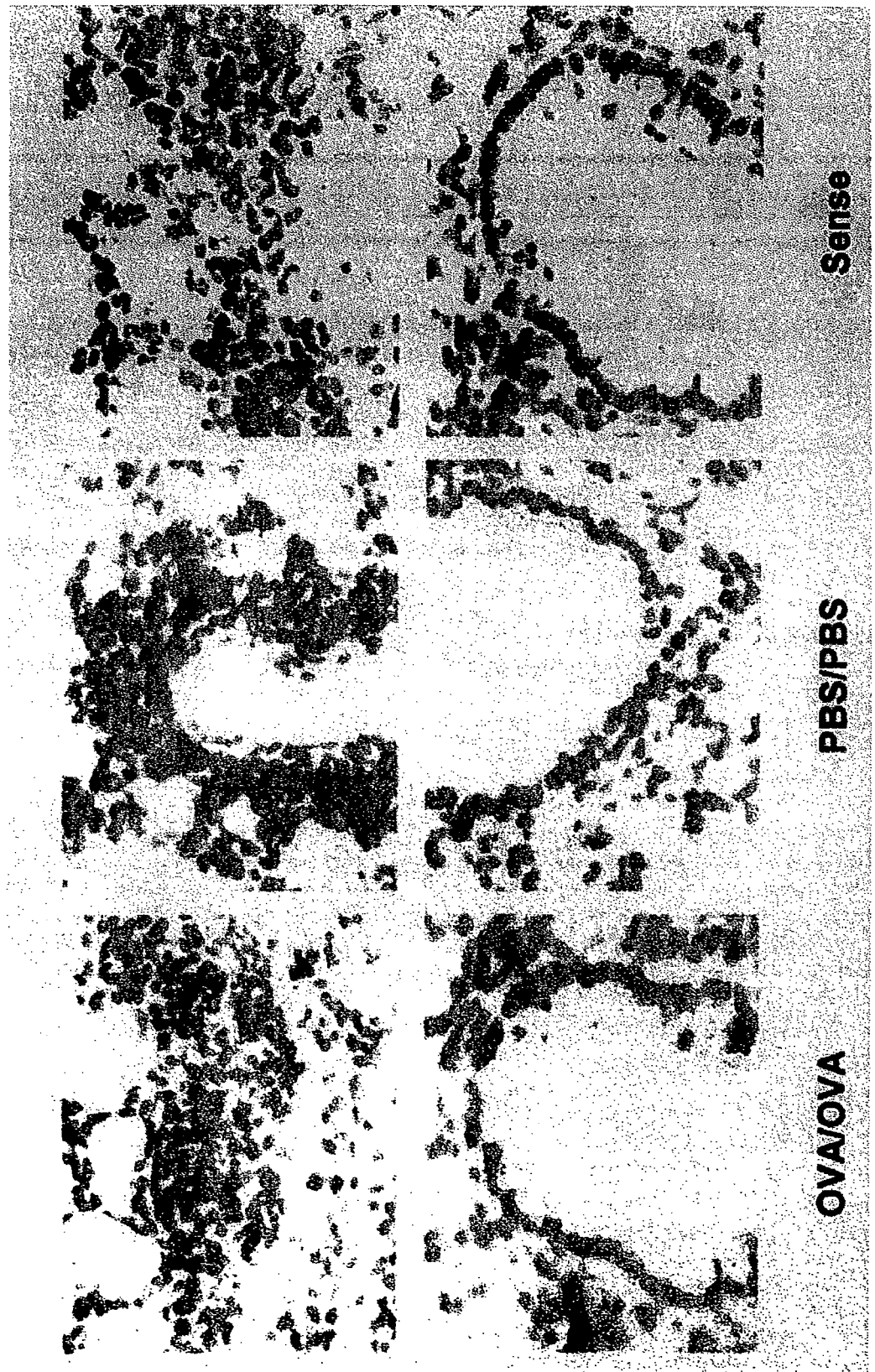
FIG. 4. In situ hybridization of murine ALX in lung. Murine $LXA_4$ receptor expression was detected in perivascular leukocyte-rich infiltrates (upper panels) and airway epithelia (lower panels) in OVA sensitized and aerosol challenged (OVA/OVA) mouse lung (representative bright-field images, magnification ×400, n=3). Experimental (PBS/PBS) and sense probe controls are shown for comparison.
Figure 5B:
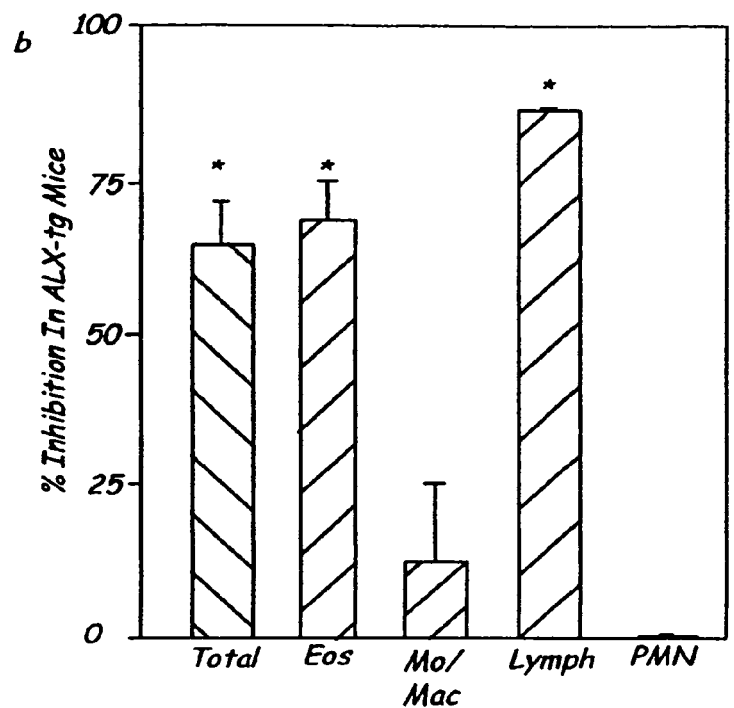
FIG. 5. Expression of human ALX in transgenic mice decreases pulmonary inflammation. a, Lung histopathology from human ALX transgenic mice. Non-transgenic (left column) and human ALX-tg mice (right column) were sensitized and aerosol challenged with OVA. Representative (n=6) lung tissue sections (magnifications: ×100 (a,b) and ×200 (c,d)) were obtained from formalin-fixed, paraffin-embedded lung tissue, prepared and stained with hematoxylin and eosin. br, bronchus; v, vessel. b-e, BAL fluids were obtained, leukocytes enumerated and identified after Wright-Giemsa stain. Percent inhibition in cell number (b) and changes in mediator profile of specific cytokines and lipid mediators (c) were determined. Serum total IgE levels were determined by immunoassay in samples from mice sensitized/challenged with either OVA or buffer (PBS) (d). Airway reactivity was determined by methacholine (100 mg/ml)-dependent change in Penh (e). Results are expressed as mean±SEM (n=4, d≧2). *P<0.05 by Student's t-test compared to control animals.
Figure 5C:
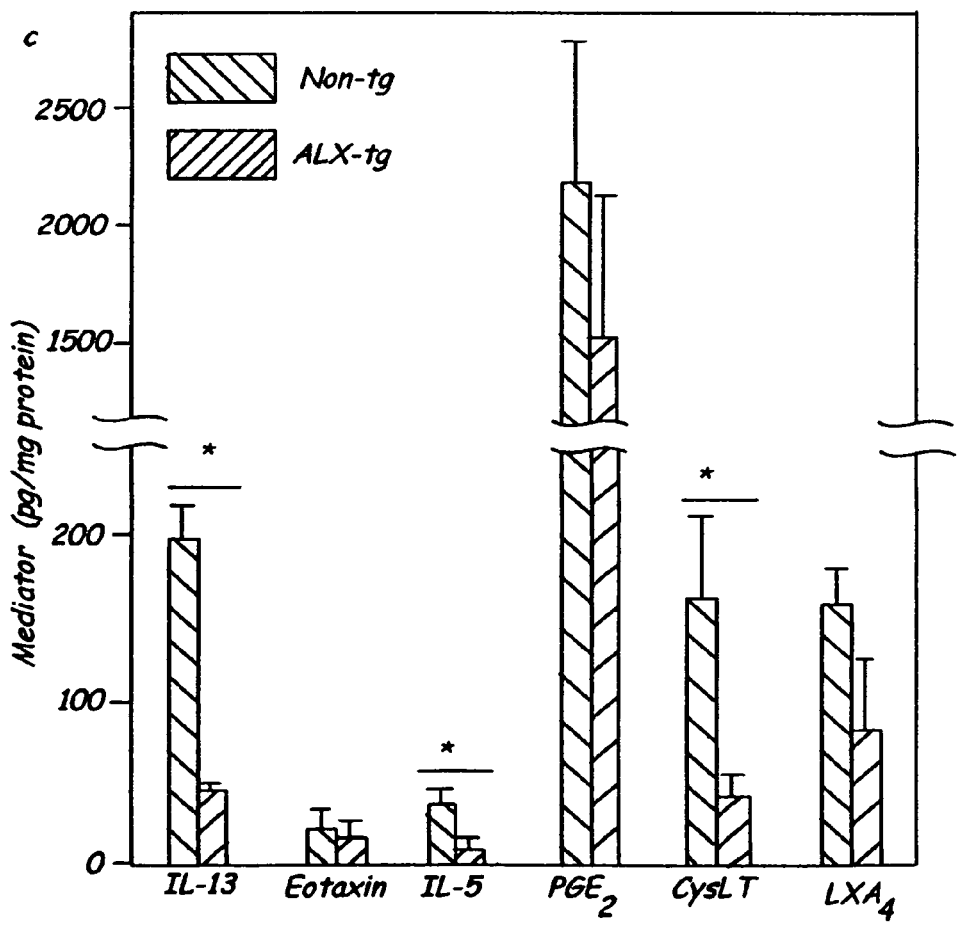
Figure 5D:
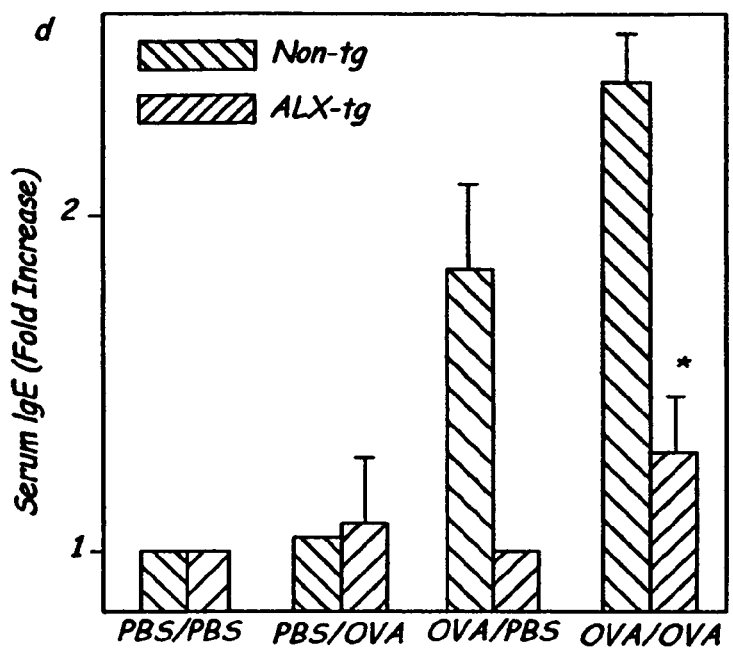
Figure 5E:
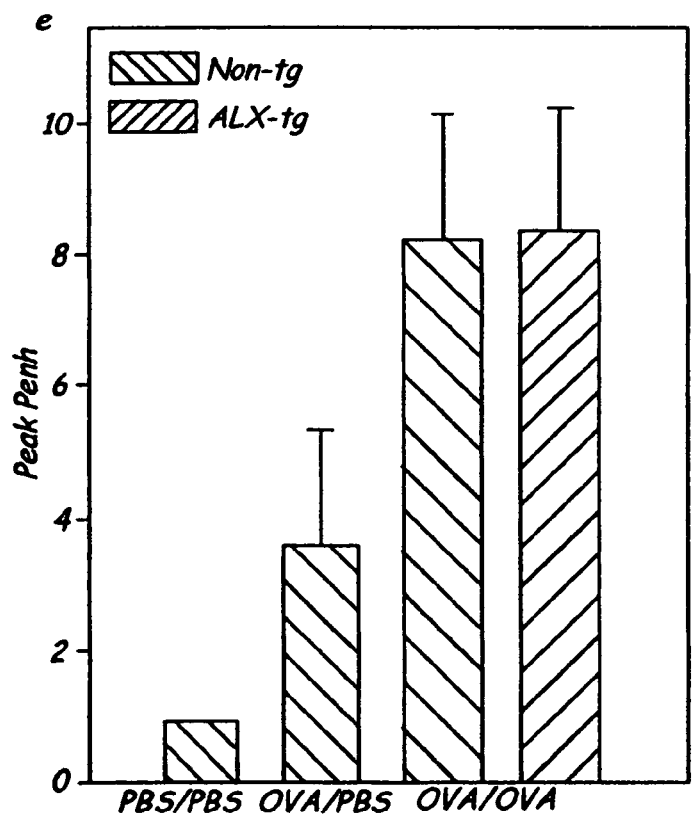

Allergen sensitization and challenge with OVA increased $LXA_4$ receptor (ALX) expression in infiltrating leukocytes and airway epithelial cells observed with in situ hybridization (FIG. 4). To assess whether OVA allergic pulmonary inflammation and airway reactivity were amenable to regulation by ALX, the responses of transgenic mice expressing human ALX using the CD11b promoter on their leukocytes (see Methods) was assessed. After OVA sensitization and aerosol challenge, human ALX transgenic animals (ALX-tg) displayed reduced airway and vascular injury, when compared to their age and gender-matched littermate controls (Non-tg). A clear decrease in leukocytic infiltrates was observed in peribronchial and perivascular spaces (FIG. 5a). BAL from allergen challenged ALX-tg mice also had reduced numbers of total leukocytes, eosinophils and lymphocytes, with 63%, 68% and 85% inhibition, respectively (FIG. 5b). Levels of several key pro-inflammatory peptide and lipid mediators were also decreased in ALX-tg mice, including IL-13 (77% inhibition), IL-5 (71% inhibition) and CysLT (74% inhibition) (FIG. 5c). In addition, allergen sensitization in the ALX-tg animals was blunted, as monitored by total serum IgE levels (FIG. 5d). Despite inhibition of allergic inflammation in the OVA sensitized and challenged ALX-tg mice, significant differences in airway hyper-responsiveness were not observed (FIG. 5e) when compared to age and gender-matched littermates (peak Penh was 8.37±1.89 (ALX-tg) and 8.25±1.90 (Non-tg), mean+/−S.E. for n=6).

Expression of Human $LXA_4$ Receptors Inhibits Murine Eosinophil Tissue Infiltration.

Figure 6:
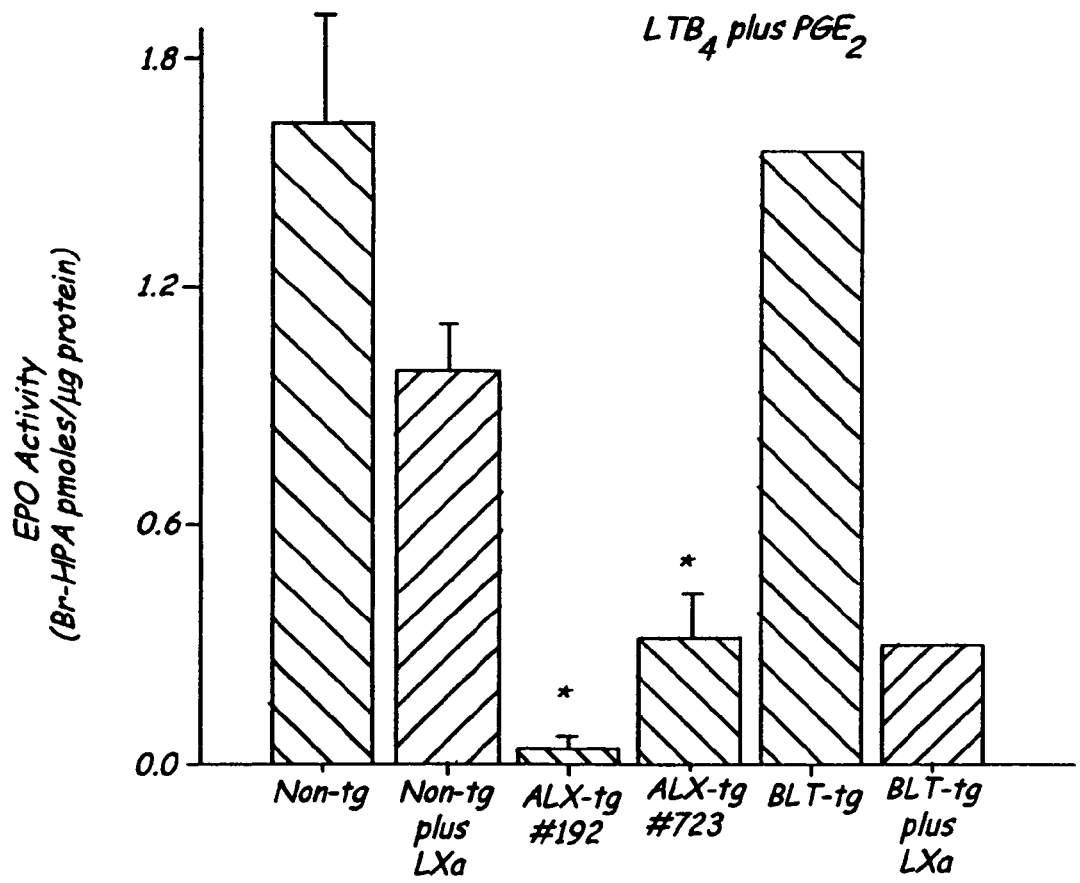
FIG. 6. Expression of human ALX in transgenic mice prevents eosinophil trafficking. $LTB_4$ (1 μg) and $PGE_2$ (1 μg) were topically applied (13-16 h) to mouse ear skin and EPO activity in tissue biopsies was determined by bromination of HPA (see Methods). Values represent the mean±SEM for pmoles Br-HPA per μg total protein for Non-tg littermates (n=6) or BLT-tg (n=2) mice in the absence or presence of topical LXa (10 μg per ear) and 2 separate ALX-tg lines (n=4). *P<0.05 by Student's T-test compared to littermate controls.

With levels of both tissue leukocytes and pro-inflammatory mediators reduced in allergic ALX-tg mouse lungs (FIG. 5), the direct impact of human ALX expression on murine eosinophil recruitment in vivo was examined. After topical application of $LTB_4$ (1 µg) and $PGE_2$ (1 µg) to mouse ear skin, there was a significant increase in eosinophil tissue infiltration as quantified by eosinophil peroxidase (EPO) activity present within 6 mm skin punch biopsies (FIG. 6). Compared to littermate non-tg controls, expression of human ALX markedly reduced the number of eosinophils recruited in ear skin tissues from two separate murine transgenic lines (FIG. 6). Of note, endogenous $LXA_4$ was recovered from inflamed ears and was without significantly different levels between ALX-tg and Non-tg animals (16.0+/−1.5 and 11.5+/−1.9 pg/mg protein, respectively). Increased expression of human $LTB_4$ receptors on leukocytes (also using CD11b promoter) led to a similar amplitude of eosinophil infiltration in this model as Non-tg littermate controls. Topical administration of as little LXa as 10 µg to mouse ears inhibited eicosanoid-stimulated skin EPO activity in both Non-tg mice as well as those with increased expression of $LTB_4$ receptors (FIG. 6). Together, these findings indicate that $LXA_4$-ALX interactions can mediate potent inhibition of eosinophil responses in vivo.

Sensitization and Challenge Protocols

Five to seven week old male FVB (Charles River Laboratories, Wilmington, Mass.) mice were housed in isolation cages under viral antibody-free conditions. After Harvard Medical Area IRB approval (Protocol #02570), mice were sensitized with intraperitoneal injections of ovalbumin (OVA) (Grade III; Sigma Chemical Co., St. Louis, Mo.) (10 mg) plus 1 mg aluminum hydroxide (ALUM) (J. T. Baker Chemical Co.; Phillipsburg, N.J.) as adjuvant in 0.2 ml PBS on days 0 and 7. On days 14, 15, 16 and 17, the mice received an analog of $LXA_4$ (15-epi,16-para-fluoro-phenoxy-$LXA_4$-methyl ester) (10 mg, 21.7 nmoles), montelukast (13 mg, 21.7 nmoles) or PBS with 1.6 mM $CaCl_2$ and 1.6 mM $MgCl_2$ (0.1 ml) by intravenous injection at least 1 h prior to an aerosol challenge containing either PBS or 6% OVA for 25 min/day. On day 18, 24 h after the last aerosol challenge, bilateral bronchoalveolar lavage (BAL) (2 aliquots of 1 ml PBS plus 0.6 mM EDTA) was performed. BAL fluids were centrifuged (2000 g, 10 min) and cells were resuspended in HBSS, enumerated by hemocytometer, and concentrated onto microscope slides by cytocentrifuge (STATspin) (265 g). Cells were stained with a Wright-Giemsa stain (Sigma Chemical Co.) to determine leukocyte differentials (after counting >200 cells).

Figure 7:
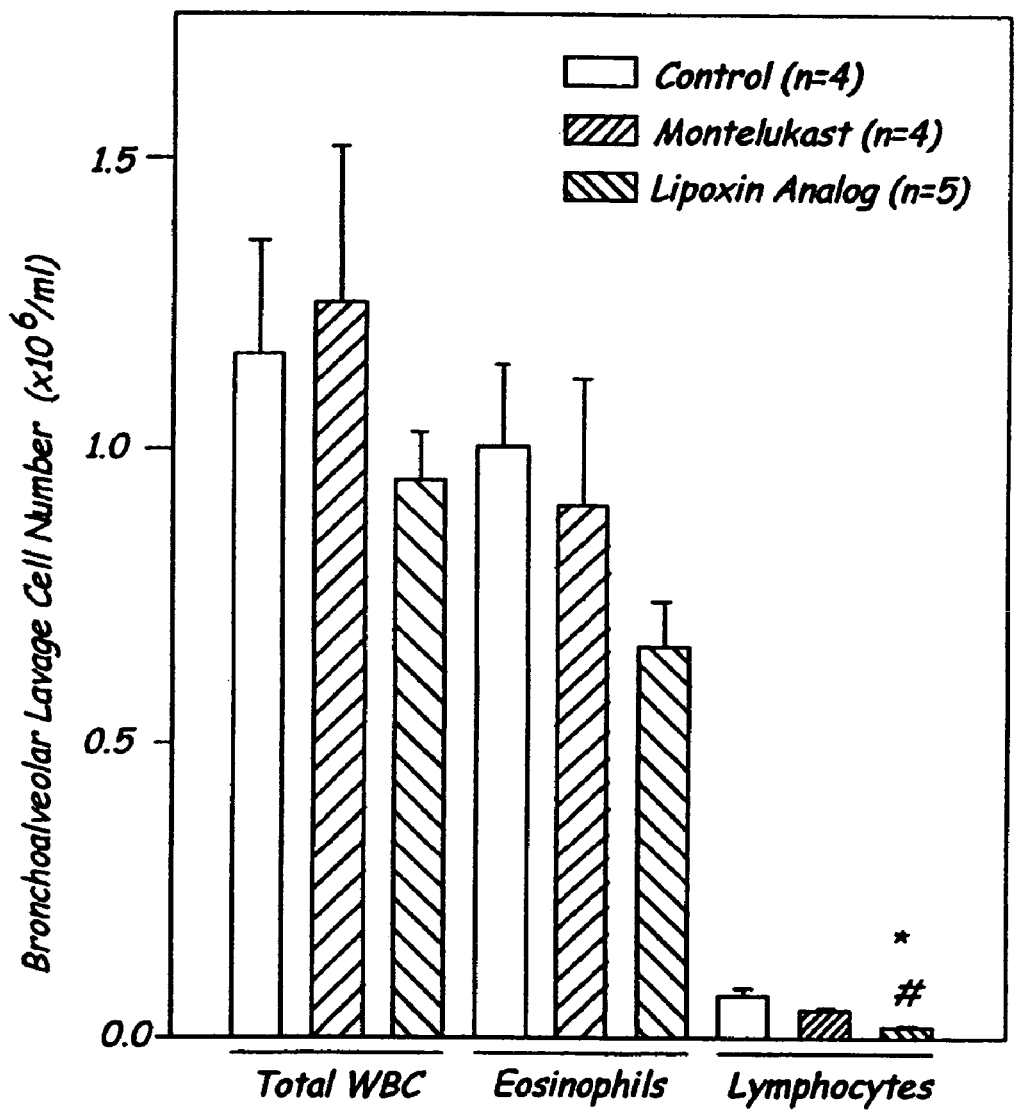
FIG. 7. Depicts regulation of allergic airway inflammation by 15-epi,16-para-fluoro-phenoxy-$LXA_4$-methyl ester in comparison to a commercially available drug (Montelukast) used to treat chronic asthma. This graph demonstrates that the $LXA_4$ methyl ester is statistically more effective than the Montelukast in terms of lymphocyte reduction.

FIG. 7. Depicts regulation of allergic airway inflammation by 15-epi,16-para-fluoro-phenoxy-$LXA_4$-methyl ester in comparison to a commercially available drug (Montelukast) used to treat chronic asthma. Montelukast is a leukotriene antagonist and is the subject of U.S. Pat. No. 5,565,473, the contents of which are incorporated herein in their entirety. FIG. 7 provides that the $LXA_4$ methyl ester is statistically more effective than Montelukast in terms of lymphocyte reduction.

As a consequence of these studies, $LXA_4$ analogs inhibit both airway hyper-responsiveness and inflammation in response to allergen sensitization and aerosol challenges in murine models of asthma. These models correlate with and are acceptable models for validation in humans and other mammals.

While the results of recent clinical trials in human asthma have challenged long held views on the relationship between airway inflammation and bronchial hyper-responsiveness[20,21], the present invention provides that LXa prevented both of these key asthma phenotypes in an experimental model of asthma, displaying a multi-pronged impact in vivo that in summation appears to give beneficial airway responses.

When this longer acting stable analog mimetic of endogenous $LXA_4$ was administered prior to OVA aerosol, airway hyper-responsiveness to methacholine as well as several measures of inflammation were markedly reduced. Indeed, pharmacologic levels of $LXA_4$ had direct effects on airway smooth muscle responses to challenge since native $LXA_4$ itself given to human asthmatics inhibits $LTC_4$-stimulated airway hyper-responsiveness[22] as well as blocks $LTD_4$-initiated constriction of airway smooth muscle in vitro[23]. In addition to $LXA_4$ analog actions on its cognate high affinity receptor (ALX), $LXA_4$ and the present analog (constructed on the aspirin-triggered 15-epimer $LXA_4$ biotemplate; denoted here as LXa) compete for binding with high affinity at $LTD_4$ recognition sites and compete at recombinant cysLT1 receptors expressed in Chinese hamster ovary cells in vitro[12]. The LX-mediated decrements in allergic mediators documented are also be responsible, in part, for the observed protection from the development of airway hyper-responsiveness to methacholine. In this regard, recombinant IL-4 and IL-13 induce airway hyper-responsiveness within hours without inflammatory cell recruitment or mucus production[24], IL-13 decreases human airway smooth muscle β-adrenergic responsiveness in vitro[25], and IL-5 and eotaxin lead to increased production of CysLT[26,27], which are potent bronchoconstrictors[28]. Taken together, these findings show that endogenous LX's produced within the local microenvironment might temporally regulate and reduce airway hyper-responsiveness via multiple sites of action in vivo to counterregulate pathways currently considered important in the genesis of this asthma phenotype, namely via inhibition of IL-5, IL-13 and CysLT-mediated actions on leukocytes, epithelia and smooth muscle.

Pulmonary eosinophilia was also sharply reduced in mice given LXa. Eosinophil recruitment to the lung in asthma is primarily a consequence of $T_H2$ lymphocyte activation[1], which was reduced by LXa as evidenced by lower levels of $T_H2$ cytokines in BAL fluid and decreased number of lymphocytes in both BAL fluid and lung tissue. $LXA_4$ may inhibit lymphocyte recruitment by competition for ALX binding with the urokinase plasminogen activator receptor, a potent lymphocyte chemoattractant[29]. In addition, $LXA_4$ directly inhibits eosinophil chemotaxis[30], and several of its stable analog mimetics block eotaxin formation in vivo in parasite animal models[31], promoting resolution of allergen-mediated pleural inflammation[32]. While endogenous LX production paralyzes splenic dendritic cell responsiveness to IL-12 and IL-12 production in the setting of microbial immunity[33], LXa administration during allergen challenge did not significantly alter IL-12 levels in BAL fluids, suggesting distinct sites of $LXA_4$ action in allergic inflammation down-stream from dendritic cells. In aggregate, the present invention provides potent inhibition by LXa and lipoxin analogs for both $T_H2$ lymphocyte and eosinophil recruitment in vivo, processes that characterize asthma pathobiology. Moreover, the capacity for LXa and lipoxin analogs to inhibit these inflammatory responses raises the likelihood that endogenous LX production serves in health as a pivotal regulatory event in airway and allergic inflammation.

LX's were generated endogenously during allergen induced airway inflammation. The amounts of $LXA_4$ recovered were similar to the levels of $LTB_4$, yet amounts of both of these eicosanoids were substantially lower than either CysLT's or $PGE_2$ within BAL of allergen challenged mice. Spatial and temporal analyses during an acute inflammatory response indicate that maximal LX levels recovered are delayed in onset compared to either LT's or PG's and concurrent with resolution, namely reduction of the exudate rather than initiation of inflammation[9]. Thus, the local levels of endogenously generated LX's after allergen challenge determined in this model reflect not only the interval of sample acquisition, but also the cell origins of the mediators present in BAL and other spatial relationships to cellular generators within the lung.

$LXA_4$ interacts with ALX to mediate leukocyte-selective effects that promote resolution[7,8]. In the present invention, allergic pulmonary inflammation was dramatically inhibited by expression of human ALX on murine leukocytes leading to marked decreases in serum total IgE, leukocyte tissue infiltration, and cytokine and lipid mediator formation. Of note, parallel decreases in bronchial hyper-responsiveness to methacholine were not observed in the ALX-tg mice. An uncoupling or dissociation of airway reactivity from inflammation per se has been uncovered in recent clinical trials[20,21] and may have resulted from restricted expression of the hALX transgene to cells expressing the CD11b promoter, namely, leukocytes and not resident tissues of the airways. Of interest, ALX-tg and Non-tg mice given LXa had similar reductions in IL-13 and CysLT. These findings suggest that the mechanisms for LXa-mediated inhibition of bronchial hyper-responsiveness following i.v. administration were distinct and likely secondary to the recently established direct interactions between LXa and recombinant CysLT1 receptors[12]. These present invention also provides that an increased ligand, as given pharmacologically via stable mimetic (LXa), or increased receptor (ALX) expression can prevent allergic pulmonary inflammation. Elucidation of endogenous regulators of LX pathways further provide insight into its role in inflammatory lung disease. Along these lines, whole blood from human aspirin-intolerant asthmatic individuals gives reduced LX biosynthetic capacity relative to aspirin-tolerant asthmatic or healthy individuals[34], which it is believed accounts, in part, for a more protracted and severe clinical course in patients with aspirin-intolerant asthma.

The present invention provides direct protective and regulatory roles for LX mimetics (lipoxin analogs of the invention) in airway hyper-responsiveness and asthmatic inflammation. In light of their ability to inhibit both of these key asthma phenotypes in vivo, LX mimetics represent a new treatment and therapeutic approach for asthma. Rather than inhibiting the actions of a single class of airway mediators to control asthma, LX (lipoxins) and their stable analogs promote resolution of inflammation via multiple mechanisms, including inhibition of leukocyte (eosinophil and lymphocyte) recruitment and activation; cytokine and chemokine production; and biosynthesis of pro-inflammatory lipid mediators, as demonstrated here, as well as by stimulating the non-phlogistic clearance of apoptotic leukocytes[35], blocking edema formation[32], and inhibiting neutrophil trafficking and functional responses[16]. Of note, LX stable analogs inhibit neutrophil responses in vivo with similar potency as corticosteroids[13]. Together, the present invention provides the profile of in vivo actions of LXa indicate that LX mimetics and related compounds could provide novel therapeutic approaches to the treatment of airway hyper-responsiveness and pulmonary inflammation in select populations of human asthmatics.

The present invention has surprisingly uncovered the ability for LX's and their analogs described herein to potently inhibit allergen-mediated pulmonary inflammation and airway hyper-responsiveness, establishing novel multi-pronged protective actions for these compounds. Moreover, these results indicate that the LX system, including LXs and ALX, plays pivotal and previously unappreciated roles in regulating allergy and pulmonary inflammation of interest in asthma and related pulmonary disorders.

The lipoxin analogs of the invention are useful in the treatment and prevention of airway inflammation, asthma and related disorders of the respiratory tract and lung, such as chronic bronchitis, bronchiectasis, eosinophilic lung diseases (including parasitic infection, idiopathic eosinophilic pneumonias and Churg-Strauss vasculitis), allergic bronchopulmonary aspergillosis, allergic inflammation of the respiratory tract (including rhinitis and sinusitis), bronchiolitis, bronchiolitis obliterans, bronchiolitis obliterans with organizing pneumonia, eosinophilic granuloma, Wegener's granulomatosis, sarcoidosis, hypersensitivity pneumonitis, idiopathic pulmonary fibrosis, pulmonary manifestations of connective tissue diseases, acute or chronic lung injury, adult respiratory distress syndrome, plus several other non-infectious, inflammatory disorders of the lung.

Additionally, lipoxin and the lipoxin analogs of the invention are useful in the inhibition and/or treatment and/or prevention of tissue injury, preservation of material for lung transplantation, lung injury associated with parasite infection(s), chronic obstructive pulmonary disease (COPD) (lipoxin and lipoxin analogs reduce lung damage from infiltrating inflammatory cells in this disease), aspirin-intolerant asthma, airway destruction and loss of function due to chronic inflammation, lung injury as a result of septic shock, and lung injury as a result of operating room-induced pumped lung syndrome (known as second-organ reperfusion injury of the lung).

For example, the lipoxin analogs of the invention are useful in the inhibition, treatment and/or prevention of: eosinophil-mediated inflammation of the lung or tissues; neutrophil-mediated inflammation of the lung; lymphocyte-mediated inflammation of the lung; cytokine and chemokine production, including interleukin-5, interleukin-13 and eotaxin; lipid mediator generation, including prostaglandin $E_2$ and cysteinyl leukotrienes; airway hyper-responsiveness; and airway and vascular inflammation.

The lipoxins are lipoxygenase interaction products or are based on such products. By definition, the lipoxins include a conjugated tetraene containing structure and three alcohol groups as defining features in this class of compounds. The lipoxygenase/lipoxygenase interactions are brought about during cell-cell interactions, and are exemplified by cells carrying 5-lipoxygenase that could interact with either 15-lipoxygenase bearing cells, or 12-lipoxygenase bearing cells in vivo to generate lipoxins. The stereochemistry at the C15 position are of the S configuration. More recently it was discovered that cyclooxygenase, which is inhibited by aspirin and non-steroidal anti-inflammatory drugs, and is also involved in the generation of prostanoids, can play a role in the generation of novel class of tetraene containing compounds, which have been isolated structurally elucidated, namely 15 epimeric form of lipoxins.

Suprisingly, with the discovery of cyclooxygenase-2 (an isoform of cyclooxygenase), that has an unusual enzymatic clef, it was discovered that acetylation of the enzyme by aspirin not only inhibits the generation of prostaglandins, but leads to continued activity of the COX-2 in its acetyleated form to convert arachidonic acid to generate 15RHETE. 15RHETE is the biosynthetic pre-cursor that is converted by neutrophils to 15-epi lipoxins. Again, these compounds are cell cell interaction products that are generated by a unique biosynthetic route, namely the acetylation of cyclooxygenase-2 by aspirin and its conversion of arachidonic acid to endogenous mediators that mimic the action of natural lipoxins.

These are what have been termed "aspirin triggered 15-epi lipoxins" or lipoxins that carry the alcohol group in the C15 position and the R configuration. The distinction between these two biochemical pathways, namely LO-LO interaction versus cyclooxygenase-2 and LO interaction provides some inferences as to the local mediator roles of these compounds and where there may be effective as endogenous biological agents to regulate/down regulate pro-inflammatory processes in vivo. The design and discovery of analogs based on these structures, at present appear to have similar biological actions and serve as mimetics of the natural lipoxins. However, in the not to distant future, it may become apparent that the aspirin COX-2 triggered pathway may have a unique profile of actions, namely actions that are specific for 15-epi lipoxins versus natural lipoxins. Setting a barrier between these two geniuses should not only reflect the chemical structures, but also their biosynthetic origins and potential role in human and mammalian biology and pharmacology.

In one embodiment, lipoxin analogs useful in the invention have the formula (I)

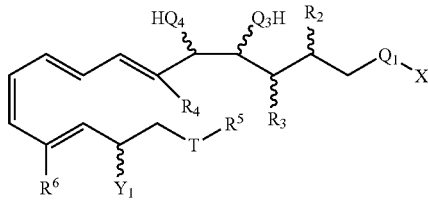

wherein X is $R_1$, $OR_1$, or $SR_1$;
wherein $R_1$ is
(i) a hydrogen atom;
(ii) an alkyl of 1 to 8 carbon atoms, inclusive, which may be straight chain or branched;
(iii) a cycloalkyl of 3 to 10 carbon atoms;
(iv) an aralkyl of 7 to 12 carbon atoms;
(v) phenyl;
(vi) substituted phenyl

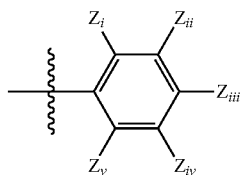

wherein $Z_i$, $Z_{ii}$, $Z_{iii}$, $Z_{iv}$ and $Z_v$ are each independently selected from —$NO_2$, —CN, —C(=O)—$R_1$, —$SO_3H$, a hydrogen atom, halogen, methyl, —$OR_x$, wherein $R_x$ is 1 to 8 carbon atoms, inclusive, which may be a straight chain or branched, and hydroxyl;
(vii) a detectable label molecule; or
(viii) a straight or branched chain alkenyl of 2 to 8 carbon atoms, inclusive;
wherein $Q_1$ is (C=O), $SO_2$ or (CN), provided when $Q_1$ is CN, then X is absent;
wherein $Q_3$ and $Q_4$ are each independently O, S or NH;
wherein one of $R_2$ and $R_3$ is a hydrogen atom and the other is
(a) H;
(b) an alkyl of 1 to 8 carbon atoms, inclusive, which may be a straight chain or branched;
(c) a cycloalkyl of 3 to 6 carbon atoms, inclusive;
(d) an alkenyl of 2 to 8 carbon atoms, inclusive, which may be straight chain or branched; or
(e) $R_aQ_2R_b$ wherein $Q_2$ is —O— or —S—; wherein $R_a$ is alkylene of 0 to 6 carbon atoms, inclusive, which may be straight chain or branched and wherein $R_b$ is alkyl of 0 to 8 carbon atoms, inclusive, which may be straight chain or branched, provided when $R_b$ is 0, then $R_b$ is a hydrogen atom;
wherein $R_4$ is
(a) H;
(b) an alkyl of 1 to 6 carbon atoms, inclusive, which may be a straight chain or branched;
wherein $R_5$ is

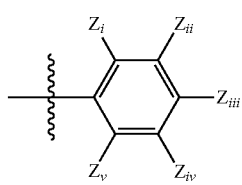

wherein $Z_i$, $Z_{ii}$, $Z_{iii}$, $Z_{iv}$ and $Z_v$ are each independently selected from —$NO_2$, —CN, —C(=O)—$R_1$, —$SO_3H$, a hydrogen atom, halogen, methyl, —$OR_x$, wherein $R_x$ is 1 to 8 carbon atoms, inclusive, which may be a straight chain or branched, and hydroxyl or a substituted or unsubstituted, branched or unbranched alkyl group;
wherein $Y_1$ is —OH, methyl, —SH, an alkyl of 2 to 4 carbon atoms, inclusive, straight chain or branched, an alkoxy of 1 to 4 carbon atoms, inclusive, or $CH_aZ_b$ where a+b=3, a=0 to 3, b=0 to 3 and Z is cyano, nitro or a halogen;
wherein $R_6$ is
(a) H;
(b) an alkyl from 1 to 4 carbon atoms, inclusive, straight chain or branched;
wherein T is O or S, and pharmaceutically acceptable salts thereof.

In another embodiment, compounds useful in the invention have the formula (II)

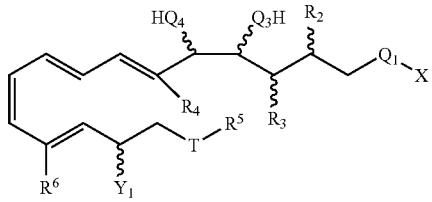

wherein X is $R_1$, $OR_1$, or $SR_1$;
wherein $R_1$ is
(i) a hydrogen atom;
(ii) an alkyl of 1 to 8 carbon atoms, inclusive, which may be straight chain or branched;
(iii) a cycloalkyl of 3 to 10 carbon atoms;
(iv) an aralkyl of 7 to 12 carbon atoms;
(v) phenyl;
(vi) substituted phenyl

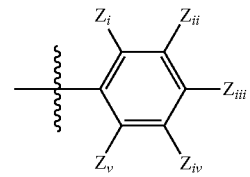

wherein $Z_i$, $Z_{ii}$, $Z_{iii}$, $Z_{iv}$ and $Z_v$ are each independently selected from —$NO_2$, —CN, —C(=O)—$R_1$, —$SO_3H$, a hydrogen atom, halogen, methyl, —$OR_x$, wherein $R_x$ is 1 to 8 carbon atoms, inclusive, which may be a straight chain or branched, and hydroxyl;
(vii) a detectable label molecule; or
(viii) a straight or branched chain alkenyl of 2 to 8 carbon atoms, inclusive;
wherein $Q_1$ is (C=O), $SO_2$ or (CN), provided when $Q_1$ is CN, then X is absent;
wherein one of $R_2$ and $R_3$ is a hydrogen atom and the other is
(a) H;
(b) an alkyl of 1 to 8 carbon atoms, inclusive, which may be a straight chain or branched;
(c) a cycloalkyl of 3 to 6 carbon atoms, inclusive;
(d) an alkenyl of 2 to 8 carbon atoms, inclusive, which may be straight chain or branched; or
(e) $R_aQ_2R_b$ wherein $Q_2$ is —O— or —S—; wherein $R_a$ is alkylene of 0 to 6 carbon atoms, inclusive, which may be straight chain or branched and wherein $R_b$ is alkyl of 0 to 8 carbon atoms, inclusive, which may be straight chain or branched, provided when $R_b$ is 0, then $R_b$ is a hydrogen atom;

wherein $R_4$ is
(a) H;
(b) an alkyl of 1 to 6 carbon atoms, inclusive, which may be a straight chain or branched;
wherein $R_5$ is

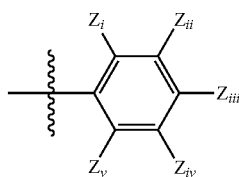

wherein $Z_i$, $Z_{ii}$, $Z_{iii}$, $Z_{iv}$ and $Z_v$ are each independently selected from $-NO_2$, $-CN$, $-C(=O)-R_1$, $-SO_3H$, a hydrogen atom, halogen, methyl, $-OR_x$, wherein $R_x$ is 1 to 8 carbon atoms, inclusive, which may be a straight chain or branched, and hydroxyl or a substituted or unsubstituted, branched or unbranched alkyl group;
wherein $Y_1$ is $-OH$, methyl, $-SH$, an alkyl of 2 to 4 carbon atoms, inclusive, straight chain or branched, an alkoxy of 1 to 4 carbon atoms, inclusive, or $CH_aZ_b$ where a+b=3, a=0 to 3, b=0 to 3 and Z is cyano, nitro or a halogen;
wherein $R_6$ is
(a) H;
(b) an alkyl from 1 to 4 carbon atoms, inclusive, straight chain or branched;
wherein T is O or S, and pharmaceutically acceptable salts thereof.

The invention is also directed to useful lipoxin compounds having the formula (III)

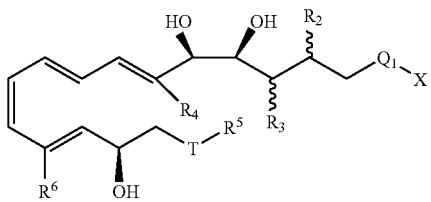

wherein X is $R_1$, $OR_1$, or $SR_1$;
wherein $R_1$ is
(i) a hydrogen atom;
(ii) an alkyl of 1 to 8 carbon atoms, inclusive, which may be straight chain or branched;
(iii) a cycloalkyl of 3 to 10 carbon atoms;
(iv) an aralkyl of 7 to 12 carbon atoms;
(v) phenyl;
(vi) substituted phenyl

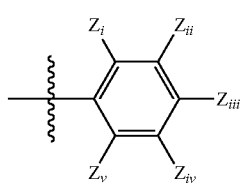

wherein $Z_i$, $Z_{ii}$, $Z_{iii}$, $Z_{iv}$ and $Z_v$ are each independently selected from $-NO_2$, $-CN$, $-C(=O)-R_1$, $-SO_3H$, a hydrogen atom, halogen, methyl, $-OR_x$, wherein $R_x$ is 1 to 8 carbon atoms, inclusive, which may be a straight chain or branched, and hydroxyl;
(vii) a detectable label molecule; or
(viii) a straight or branched chain alkenyl of 2 to 8 carbon atoms, inclusive;
wherein $Q_1$ is (C=O), $SO_2$ or (CN), provided when $Q_1$ is CN, then X is absent;
wherein one of $R_2$ and $R_3$ is a hydrogen atom and the other is
(a) H;
(b) an alkyl of 1 to 8 carbon atoms, inclusive, which may be a straight chain or branched;
(c) a cycloalkyl of 3 to 6 carbon atoms, inclusive;
(d) an alkenyl of 2 to 8 carbon atoms, inclusive, which may be straight chain or branched; or
(e) $R_aQ_2R_b$ wherein $Q_2$ is $-O-$ or $-S-$; wherein $R_a$ is alkylene of 0 to 6 carbon atoms, inclusive, which may be straight chain or branched and wherein $R_b$ is alkyl of 0 to 8 carbon atoms, inclusive, which may be straight chain or branched, provided when $R_b$ is 0, then $R_b$ is a hydrogen atom;
wherein $R_4$ is
(a) H;
(b) an alkyl of 1 to 6 carbon atoms, inclusive, which may be a straight chain or branched;
wherein $R_5$ is

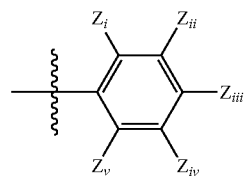

wherein $Z_i$, $Z_{ii}$, $Z_{iii}$, $Z_{iv}$ and $Z_v$ are each independently selected from $-NO_2$, $-CN$, $-C(=O)-R_1$, $-SO_3H$, a hydrogen atom, halogen, methyl, $-OR_x$, wherein $R_x$ is 1 to 8 carbon atoms, inclusive, which may be a straight chain or branched, and hydroxyl or a substituted or unsubstituted, branched or unbranched alkyl group;
wherein $R_6$ is
(a) H;
(b) an alkyl from 1 to 4 carbon atoms, inclusive, straight chain or branched;
wherein T is O or S, and pharmaceutically acceptable salts thereof.

The invention is further directed to useful lipoxin compounds having the formula (IV)

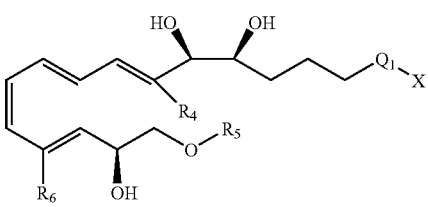

wherein X is $R_1$, $OR_1$, or $SR_1$;
wherein $R_1$ is
(i) a hydrogen atom;
(ii) an alkyl of 1 to 8 carbon atoms, inclusive, which may be straight chain or branched;

(iii) a cycloalkyl of 3 to 10 carbon atoms;
(iv) an aralkyl of 7 to 12 carbon atoms;
(v) phenyl;
(vi) substituted phenyl

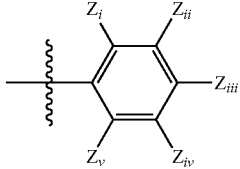

wherein $Z_i$, $Z_{ii}$, $Z_{iii}$, $Z_{iv}$ and $Z_v$ are each independently selected from —$NO_2$, —CN, —C(=O)—$R_1$, —$SO_3H$, a hydrogen atom, halogen, methyl, —$OR_x$, wherein $R_x$ is 1 to 8 carbon atoms, inclusive, which may be a straight chain or branched, and hydroxyl;
(vii) a detectable label molecule; or
(viii) a straight or branched chain alkenyl of 2 to 8 carbon atoms, inclusive;
wherein $Q_1$ is (C=O), $SO_2$ or (CN), provided when $Q_1$ is CN, then X is absent;
wherein $R_4$ is
(a) H;
(b) an alkyl of 1 to 6 carbon atoms, inclusive, which may be a straight chain or branched;
wherein $R_5$ is

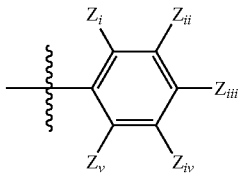

wherein $Z_i$, $Z_{ii}$, $Z_{iii}$, $Z_{iv}$ and $Z_v$ are each independently selected from —$NO_2$, —CN, —C(=O)—$R_1$, —$SO_3H$, a hydrogen atom, halogen, methyl, —$OR_x$, wherein $R_x$ is 1 to 8 carbon atoms, inclusive, which may be a straight chain or branched, and hydroxyl or a substituted or unsubstituted, branched or unbranched alkyl group;
wherein $R_6$ is
(a) H;
(b) an alkyl from 1 to 4 carbon atoms, inclusive, straight chain or branched;
wherein T is O or S, and pharmaceutically acceptable salts thereof.

The invention is further directed to useful lipoxin compounds having the formula (V)

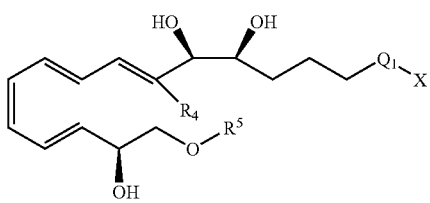

wherein X is $R_1$, $OR_1$, or $SR_1$;
wherein $R_1$ is
(i) a hydrogen atom;
(ii) an alkyl of 1 to 8 carbon atoms, inclusive, which may be straight chain or branched;

(iii) a cycloalkyl of 3 to 10 carbon atoms;
(iv) an aralkyl of 7 to 12 carbon atoms;
(v) phenyl;
(vi) substituted phenyl

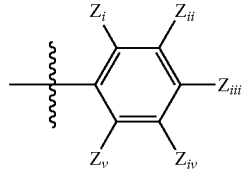

wherein $Z_i$, $Z_{ii}$, $Z_{iii}$, $Z_{iv}$ and $Z_v$ are each independently selected from —$NO_2$, —CN, —C(=O)—$R_1$, —$SO_3H$, a hydrogen atom, halogen, methyl, —$OR_x$, wherein $R_x$ is 1 to 8 carbon atoms, inclusive, which may be a straight chain or branched, and hydroxyl;
(vii) a detectable label molecule; or
(viii) a straight or branched chain alkenyl of 2 to 8 carbon atoms, inclusive;
wherein $R_4$ is
(a) H;
(b) an alkyl of 1 to 6 carbon atoms, inclusive, which may be a straight chain or branched;
wherein $R_5$ is

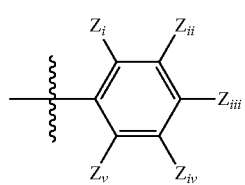

wherein $Z_i$, $Z_{ii}$, $Z_{iii}$, $Z_{iv}$ and $Z_v$ are each independently selected from —$NO_2$, —CN, —C(=O)—$R_1$, —$SO_3H$, a hydrogen atom, halogen, methyl, —$OR_x$, wherein $R_x$ is 1 to 8 carbon atoms, inclusive, which may be a straight chain or branched, and hydroxyl or a substituted or unsubstituted, branched or unbranched alkyl group; and
pharmaceutically acceptable salts thereof.

In certain embodiments, X is $OR_1$ wherein $R_1$ is a hydrogen atom, an alkyl group of 1 to 4 carbon atoms or a pharmaceutically acceptable salt, $Q_1$ is C=O, $R_2$ and $R_3$, if present, are hydrogen atoms, $R_4$ is a hydrogen atom or methyl, $Q_3$ and $Q_4$, if present, are both O, $R_6$, if present, is a hydrogen atom, $Y_1$, if present, is OH, T is O and $R_5$ is a substituted phenyl, e.g.,

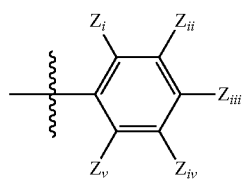

wherein $Z_i$, $Z_{ii}$, $Z_{iii}$, $Z_{iv}$ and $Z_v$ are each independently selected from —$NO_2$, —CN, —C(=O)—$R_1$, —$SO_3H$, a hydrogen atom, halogen, methyl, —$OR_x$, wherein $R_x$ is 1 to 8 carbon atoms, inclusive, which may be a straight chain or branched, and hydroxyl. In certain embodiments for $R_5$, para-fluorophenyl and/or unsubstituted phenyl are optimal, e.g., 15-epi-16-(para-fluoro)-phenoxy-LXA$_4$, 16-(para-fluoro)-phenoxy-LXA$_4$, 15-epi-16-phenoxy-LXA$_4$ or 16-phenoxy-LXA$_4$. The compounds encompassed by U.S. Pat. No. 5,441,951 are excluded from certain aspects of the present invention.

In still another aspect, the present invention is directed to pharmaceutical compositions including compounds having the above-described formulae and a pharmaceutically acceptable carrier. In one embodiment, the compound is

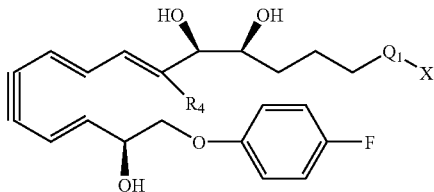

In certain embodiments, $Y_1$ is a hydroxyl and the carbon bearing the hydroxyl can have an R or S configuration. In most embodiments, the chiral carbon bearing the hydroxyl group, e.g., $Y_1$, is designated as a 15-epi-lipoxin as is known in the art.

In certain embodiments the chirality of the carbons bearing the $R_2$, $R_3$, $Q_3$ and $Q_4$ groups can each independently be either R or S. In certain embodiments, $Q_3$ and $Q_4$ have the chiralities shown in structures II, III, IV or V.

In certain embodiments, $R_4$ is a hydrogen. In other embodiments, $R_6$ is a hydrogen.

Additionally, $R_5$ can be a substituted or unsubstituted, branched or unbranched alkyl group having between 1 and about 6 carbon atoms, preferably between 1 and 4 carbon atoms, most preferably between 1 and 3, and preferably one or two carbon atoms. The carbon atoms can have substituents which include halogen atoms, hydroxyl groups, or ether groups.

The compounds useful in the present invention can be prepared by the following synthetic scheme:

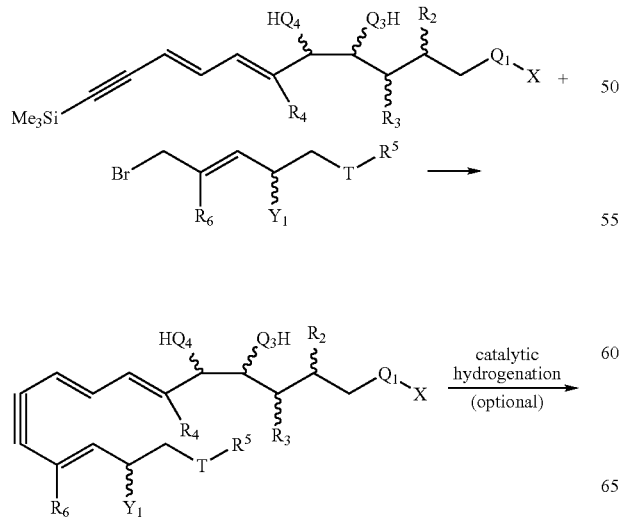

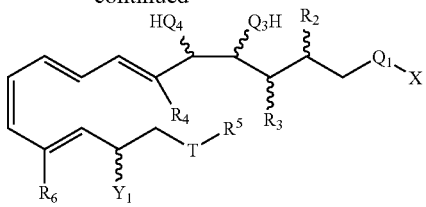

wherein X, $Q_1$, $Q_3$, $Q_4$, $R_2$, $R_3$, $R_4$, $R_5$, $R_6$, $Y_1$ and T are as defined above. Suitable methods known in the art to can be used to produce each fragment. For example, the acetylenic fragment can be prepared by the methods discussed in Nicolaou, K. C. et al. (1991) Angew. Chem. Int. Ed. Engl. 30:1100; Nicolaou, K. C. et al. (1989) J. Org. Chem. 54:5527; Webber, S. E. et al. (1988) Adv. Exp. Med. Biol. 229:61; and U.S. Pat. No. 5,441,951. The second fragment can be prepared by the methods of Raduchel, B. and Vorbruggen, H. (1985) Adv. Prostaglandin Thromboxane Leukotriene Res. 14:263.

In another embodiment, compounds useful in the invention have the formula (VI)

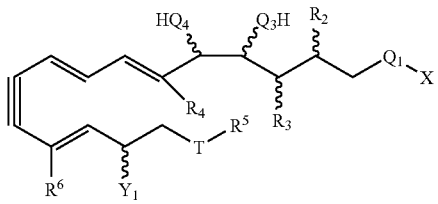

wherein X is $R_1$, $OR_1$, or $SR_1$;
wherein $R_1$ is
(i) a hydrogen atom;
(ii) an alkyl of 1 to 8 carbon atoms, inclusive, which may be straight chain or branched;
(iii) a cycloalkyl of 3 to 10 carbon atoms;
(iv) an aralkyl of 7 to 12 carbon atoms;
(v) phenyl;
(vi) substituted phenyl

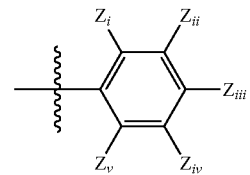

wherein $Z_i$, $Z_{ii}$, $Z_{iii}$, $Z_{iv}$ and $Z_v$ are each independently selected from —NO$_2$, —CN, —C(=O)—R$_1$, —SO$_3$H, a hydrogen atom, halogen, methyl, —OR$_x$, wherein R$_x$ is 1 to 8 carbon atoms, inclusive, which may be a straight chain or branched, and hydroxyl;
(vii) a detectable label molecule; or
(viii) a straight or branched chain alkenyl of 2 to 8 carbon atoms, inclusive;
wherein $Q_1$ is (C=O), SO$_2$ or (CN), provided when $Q_1$ is CN, then X is absent;
wherein $Q_3$ and $Q_4$ are each independently O, S or NH;
wherein one of $R_2$ and $R_3$ is a hydrogen atom and the other is
(a) H;
(b) an alkyl of 1 to 8 carbon atoms, inclusive, which may be a straight chain or branched;

(c) a cycloalkyl of 3 to 6 carbon atoms, inclusive;
(d) an alkenyl of 2 to 8 carbon atoms, inclusive, which may be straight chain or branched; or
(e) $R_a Q_2 R_b$ wherein $Q_2$ is —O— or —S—; wherein $R_a$ is alkylene of 0 to 6 carbon atoms, inclusive, which may be straight chain or branched and wherein $R_b$ is alkyl of 0 to 8 carbon atoms, inclusive, which may be straight chain or branched, provided when $R_b$ is 0, then $R_b$ is a hydrogen atom;

wherein $R_4$ is
(a) H;
(b) an alkyl of 1 to 6 carbon atoms, inclusive, which may be a straight chain or branched;

wherein $R_5$ is

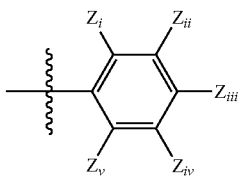

wherein $Z_i$, $Z_{ii}$, $Z_{iii}$, $Z_{iv}$ and $Z_v$ are each independently selected from —$NO_2$, —CN, —C(=O)—$R_1$, —$SO_3H$, a hydrogen atom, halogen, methyl, —$OR_x$, wherein $R_x$ is 1 to 8 carbon atoms, inclusive, which may be a straight chain or branched, and hydroxyl or a substituted or unsubstituted, branched or unbranched alkyl group;

wherein $Y_1$ is —OH, methyl, —SH, an alkyl of 2 to 4 carbon atoms, inclusive, straight chain or branched, an alkoxy of 1 to 4 carbon atoms, inclusive, or $CH_a Z_b$ where a+b=3, a=0 to 3, b=0 to 3 and Z is cyano, nitro or a halogen;

wherein $R_6$ is
(a) H;
(b) an alkyl from 1 to 4 carbon atoms, inclusive, straight chain or branched;

wherein T is O or S, and pharmaceutically acceptable salts thereof.

It should be understood that the depictions of the acetylenic portion of the lipoxin compounds described throughout this specification are drawn for convenience and not as actual representation of bond angles.

In another embodiment, compounds useful in the invention have the formula (VII)

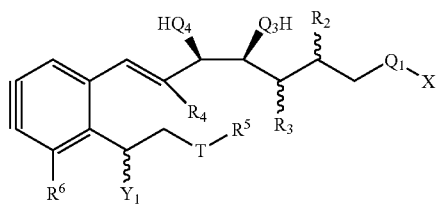

wherein X is $R_1$, $OR_1$, or $SR_1$;
wherein $R_1$ is
(i) a hydrogen atom;
(ii) an alkyl of 1 to 8 carbon atoms, inclusive, which may be straight chain or branched;
(iii) a cycloalkyl of 3 to 10 carbon atoms;
(iv) an aralkyl of 7 to 12 carbon atoms;
(v) phenyl;
(vi) substituted phenyl

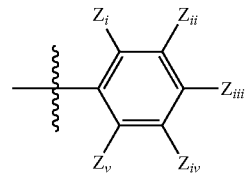

wherein $Z_i$, $Z_{ii}$, $Z_{iii}$, $Z_{iv}$ and $Z_v$ are each independently selected from —$NO_2$, —CN, —C(=O)—$R_1$, —$SO_3H$, a hydrogen atom, halogen, methyl, —$OR_x$, wherein $R_x$ is 1 to 8 carbon atoms, inclusive, which may be a straight chain or branched, and hydroxyl;
(vii) a detectable label molecule; or
(viii) a straight or branched chain alkenyl of 2 to 8 carbon atoms, inclusive;

wherein $Q_1$ is (C=O), $SO_2$ or (CN), provided when $Q_1$ is CN, then X is absent;

wherein one of $R_2$ and $R_3$ is a hydrogen atom and the other is
(a) H;
(b) an alkyl of 1 to 8 carbon atoms, inclusive, which may be a straight chain or branched;
(c) a cycloalkyl of 3 to 6 carbon atoms, inclusive;
(d) an alkenyl of 2 to 8 carbon atoms, inclusive, which may be straight chain or branched; or
(e) $R_a Q_2 R_b$ wherein $Q_2$ is —O or —S—; wherein $R_a$ is alkylene of 0 to 6 carbon atoms, inclusive, which may be straight chain or branched and wherein $R_b$ is alkyl of 0 to 8 carbon atoms, inclusive, which may be straight chain or branched, provided when $R_b$ is 0, then $R_b$ is a hydrogen atom;

wherein $R_4$ is
(a) H;
(b) an alkyl of 1 to 6 carbon atoms, inclusive, which may be a straight chain or branched;

wherein $R_5$ is

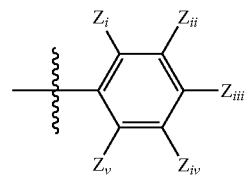

wherein $Z_i$, $Z_{ii}$, $Z_{iii}$, $Z_{iv}$ and $Z_v$ are each independently selected from —$NO_2$, —CN, —C(=O)—$R_1$, —$SO_3H$, a hydrogen atom, halogen, methyl, —$OR_x$, wherein $R_x$ is 1 to 8 carbon atoms, inclusive, which may be a straight chain or branched, and hydroxyl or a substituted or unsubstituted, branched or unbranched alkyl group;

wherein $Y_1$ is —OH, methyl, —SH, an alkyl of 2 to 4 carbon atoms, inclusive, straight chain or branched, an alkoxy of 1 to 4 carbon atoms, inclusive, or $CH_a Z_b$ where a+b=3, a=0 to 3, b=0 to 3 and Z is cyano, nitro or a halogen;

wherein $R_6$ is
(a) H;
(b) an alkyl from 1 to 4 carbon atoms, inclusive, straight chain or branched;

wherein T is O or S, and pharmaceutically acceptable salts thereof.

The invention is also directed to useful lipoxin compounds having the formula (VIII)

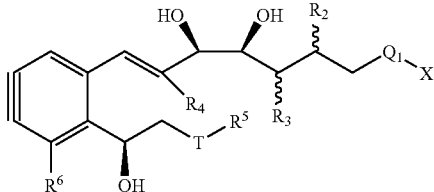

wherein X is $R_1$, $OR_1$, or $SR_1$;
wherein $R_1$ is
(i) a hydrogen atom;
(ii) an alkyl of 1 to 8 carbon atoms, inclusive, which may be straight chain or branched;
(iii) a cycloalkyl of 3 to 10 carbon atoms;
(iv) an aralkyl of 7 to 12 carbon atoms;
(v) phenyl;
(vi) substituted phenyl

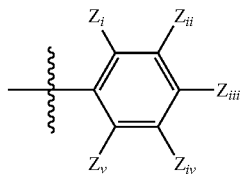

wherein $Z_i$, $Z_{ii}$, $Z_{iii}$, $Z_{iv}$ and $Z_v$ are each independently selected from —$NO_2$, —CN, —C(=O)—$R_1$, —$SO_3H$, a hydrogen atom, halogen, methyl, —$OR_x$, wherein $R_x$ is 1 to 8 carbon atoms, inclusive, which may be a straight chain or branched, and hydroxyl;
(vii) a detectable label molecule; or
(viii) a straight or branched chain alkenyl of 2 to 8 carbon atoms, inclusive;
wherein $Q_1$ is (C=O), $SO_2$ or (CN), provided when $Q_1$ is CN, then X is absent;
wherein one of $R_2$ and $R_3$ is a hydrogen atom and the other is
(a) H;
(b) an alkyl of 1 to 8 carbon atoms, inclusive, which may be a straight chain or branched;
(c) a cycloalkyl of 3 to 6 carbon atoms, inclusive;
(d) an alkenyl of 2 to 8 carbon atoms, inclusive, which may be straight chain or branched; or
(e) $R_a Q_2 R_b$ wherein $Q_2$ is —O— or —S—; wherein $R_a$ is alkylene of 0 to 6 carbon atoms, inclusive, which may be straight chain or branched and wherein $R_b$ is alkyl of 0 to 8 carbon atoms, inclusive, which may be straight chain or branched, provided when $R_b$ is 0, then $R_b$ is a hydrogen atom;
wherein $R_4$ is
(a) H;
(b) an alkyl of 1 to 6 carbon atoms, inclusive, which may be a straight chain or branched;

wherein $R_5$ is

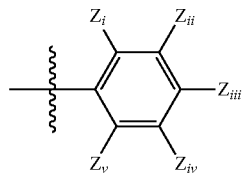

wherein $Z_i$, $Z_{ii}$, $Z_{iii}$, $Z_{iv}$ and $Z_v$ are each independently selected from —$NO_2$, —CN, —C(=O)—$R_1$, —$SO_3H$, a hydrogen atom, halogen, methyl, —$OR_x$, wherein $R_x$ is 1 to 8 carbon atoms, inclusive, which may be a straight chain or branched, and hydroxyl or a substituted or unsubstituted, branched or unbranched alkyl group;
wherein $R_6$ is
(a) H;
(b) an alkyl from 1 to 4 carbon atoms, inclusive, straight chain or branched;
wherein T is O or S, and pharmaceutically acceptable salts thereof.

The invention is further directed to useful lipoxin compounds having the formula (IX)

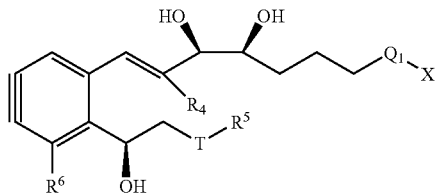

wherein X is $R_1$, $OR_1$, or $SR_1$;
wherein $R_1$ is
(i) a hydrogen atom;
(ii) an alkyl of 1 to 8 carbon atoms, inclusive, which may be straight chain or branched;
(iii) a cycloalkyl of 3 to 10 carbon atoms;
(iv) an aralkyl of 7 to 12 carbon atoms;
(v) phenyl;
(vi) substituted phenyl

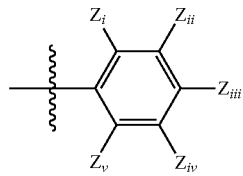

wherein $Z_i$, $Z_{ii}$, $Z_{iii}$, $Z_{iv}$ and $Z_v$ are each independently selected from —$NO_2$, —CN, —C(=O)—$R_1$, —$SO_3H$, a hydrogen atom, halogen, methyl, —$OR_x$, wherein $R_x$ is 1 to 8 carbon atoms, inclusive, which may be a straight chain or branched, and hydroxyl;
(vii) a detectable label molecule; or
(viii) a straight or branched chain alkenyl of 2 to 8 carbon atoms, inclusive;
wherein $Q_1$ is (C=O), $SO_2$ or (CN), provided when $Q_1$ is CN, then X is absent;
wherein $R_4$ is
(a) H;
(b) an alkyl of 1 to 6 carbon atoms, inclusive, which may be a straight chain or branched;

wherein $R_5$ is

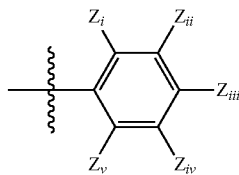

wherein $Z_i$, $Z_{ii}$, $Z_{iii}$, $Z_{iv}$ and $Z_v$ are each independently selected from —$NO_2$, —CN, —C(=O)—$R_1$, —$SO_3H$, a hydrogen atom, halogen, methyl, —$OR_x$, wherein $R_x$ is 1 to 8 carbon atoms, inclusive, which may be a straight chain or branched, and hydroxyl or a substituted or unsubstituted, branched or unbranched alkyl group;
  wherein $R_6$ is
  (a) H;
  (b) an alkyl from 1 to 4 carbon atoms, inclusive, straight chain or branched;
  wherein T is O or S, and pharmaceutically acceptable salts thereof.

The invention is further directed to useful lipoxin compounds having the formula (X)

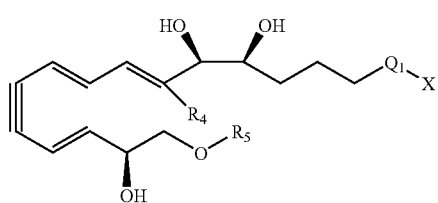

wherein X is $R_1$, $OR_1$, or $SR_1$;
wherein $R_1$ is
  (i) a hydrogen atom;
  (ii) an alkyl of 1 to 8 carbon atoms, inclusive, which may be straight chain or branched;
  (iii) a cycloalkyl of 3 to 10 carbon atoms;
  (iv) an aralkyl of 7 to 12 carbon atoms;
  (v) phenyl;
  (vi) substituted phenyl

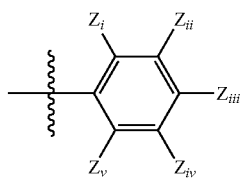

wherein $Z_i$, $Z_{ii}$, $Z_{iii}$, $Z_{iv}$ and $Z_v$ are each independently selected from —$NO_2$, —CN, —C(=O)—$R_1$, —$SO_3H$, a hydrogen atom, halogen, methyl, —$OR_x$, wherein $R_x$ is 1 to 8 carbon atoms, inclusive, which may be a straight chain or branched, and hydroxyl;
  (vii) a detectable label molecule; or
  (viii) a straight or branched chain alkenyl of 2 to 8 carbon atoms, inclusive;
wherein $R_4$ is
  (a) H;
  (b) an alkyl of 1 to 6 carbon atoms, inclusive, which may be a straight chain or branched;

wherein $R_5$ is

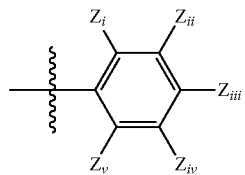

wherein $Z_i$, $Z_{ii}$, $Z_{iii}$, $Z_{iv}$ and $Z_v$ are each independently selected from —$NO_2$, —CN, —C(=O)—$R_1$, —$SO_3H$, a hydrogen atom, halogen, methyl, —$OR_x$, wherein $R_x$ is 1 to 8 carbon atoms, inclusive, which may be a straight chain or branched, and hydroxyl or a substituted or unsubstituted, branched or unbranched alkyl group; and
  pharmaceutically acceptable salts thereof.

In certain embodiments, X is $OR_1$ wherein $R_1$ is a hydrogen atom, an alkyl group of 1 to 4 carbon atoms or a pharmaceutically acceptable salt, $Q_1$ is C=O, $R_2$ and $R_3$, if present, are hydrogen atoms, $R_4$ is a hydrogen atom or methyl, $Q_3$ and $Q_4$, if present, are both O, $R_6$, if present, is a hydrogen atom, $Y_1$, if present, is OH, T is O and $R_5$ is a substituted phenyl, e.g.,

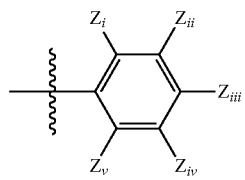

wherein $Z_i$, $Z_{ii}$, $Z_{iii}$, $Z_{iv}$ and $Z_v$ are each independently selected from —$NO_2$, —CN, —C(=O)—$R_1$, —$SO_3H$, a hydrogen atom, halogen, methyl, —$OR_x$, wherein $R_x$ is 1 to 8 carbon atoms, inclusive, which may be a straight chain or branched, and hydroxyl. In certain embodiments for $R_5$, para-fluorophenyl and/or unsubstituted phenyl acetylenic lipoxins are optimal, e.g., 15-epi-16-(para-fluoro)-phenoxy-acetylenic $LXA_4$, 16-(ara-fluoro)-phenoxy-acetylenic $LXA_4$, 15-epi-16-phenoxy-acetylenic $LXA_4$ or 16-phenoxy-acetylenic $LXA_4$. The compounds encompassed by U.S. Pat. No. 5,650,435 are excluded from certain aspects of the present invention.

In still another aspect, the present invention is directed to pharmaceutical compositions including compounds having the above-described formulae and a pharmaceutically acceptable carrier. In one embodiment, an acetylenic lipoxin is

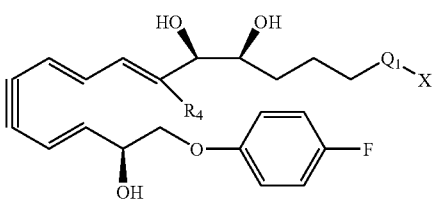

In certain embodiments, $Y_1$ is a hydroxyl and the carbon bearing the hydroxyl can have an R or S configuration. In most embodiments, the chiral carbon bearing the hydroxyl group, e.g., $Y_1$, is designated as a 15-epi-lipoxin as is known in the art.

In another embodiment, the lipoxin acetylenic analog is (XI)

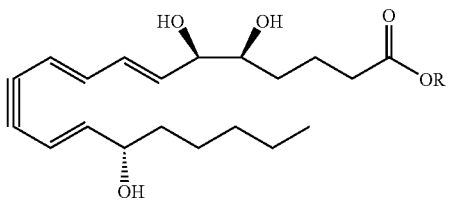

wherein R is a lower alkyl group, i.e., ethyl, methyl, a hydrogen atom, or a pharmaceutically acceptable salt. Lipoxin acetylenic analog XI had excellent anti-inflammatory properties as evidenced in FIGS. 5 and 6.

In certain embodiments the chirality of the carbons bearing the $R_2$, $R_3$, $Q_3$ and $Q_4$ groups can each independently be either R or S. In certain embodiments, $Q_3$ and $Q_4$ have the chiralities shown in structures II, III, IV or V.

In other embodiments, $R_4$ is a hydrogen. In still other embodiments, $R_6$ is a hydrogen.

Additionally, $R_5$ can be a substituted or unsubstituted, branched or unbranched alkyl group having between 1 and about 6 carbon atoms, preferably between 1 and 4 carbon atoms, most preferably between 1 and 3, and preferably one or two carbon atoms. The carbon atoms can have substituents which include halogen atoms, hydroxyl groups, or ether groups.

In particular, the lipoxins and lipoxin analogs useful for the above identified respiratory ailments include, for example:

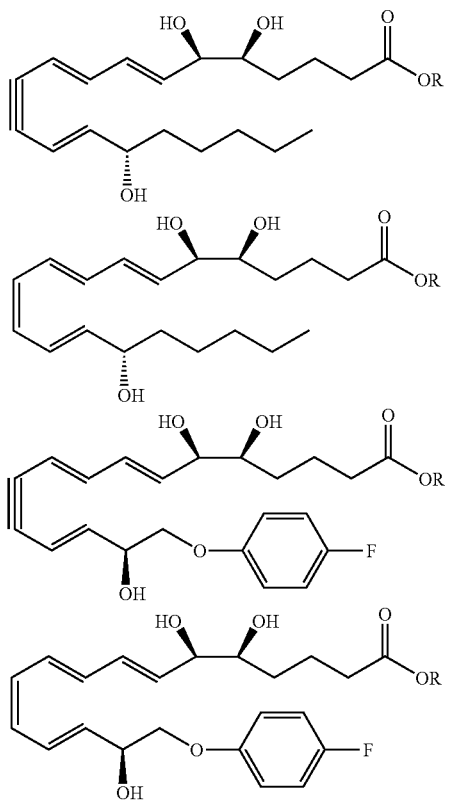

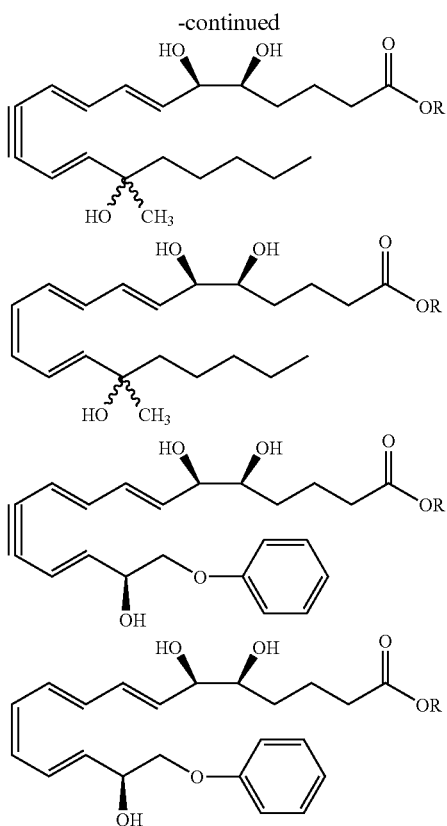

wherein R is a branched or unbranched alkyl, alkylene, or alkynyl group having 1 to 20 carbon atoms, e.g., a methyl or ethyl group, a hydrogen atom, or a pharmaceutically acceptable salt.

A "lipoxin analog" shall mean a compound which has an "active region" that functions like the active region of a "natural lipoxin", but which has a "metabolic transformation region" that differs from natural lipoxin. Lipoxin analogs include compounds which are structurally similar to a natural lipoxin, compounds which share the same receptor recognition site, compounds which share the same or similar lipoxin metabolic transformation region as lipoxin, and compounds which are art-recognized as being analogs of lipoxin. Lipoxin analogs include lipoxin analog metabolites. The compounds disclosed herein may contain one or more centers of asymmetry. Where asymmetric carbon atoms are present, more than one stereoisomer is possible, and all possible isomeric forms are intended to be included within the structural representations shown. Optically active (R) and (S) isomers may be resolved using conventional techniques known to the ordinarily skilled artisan. The present invention is intended to include the possible diastereiomers as well as the racemic and optically resolved isomers.

The terms "corresponding lipoxin" and "natural lipoxin" refer to a naturally-occurring lipoxin or lipoxin metabolite. Where an analog has activity for a lipoxin-specific receptor, the corresponding or natural lipoxin is the normal ligand for that receptor. For example, where an analog is a $LXA_4$ specific receptor on differentiated HL-60 cells, the corresponding lipoxin is $LXA_4$. Where an analog has activity as an antagonist to another compound (such as leukotriene C4 and/or leukotriene D4), which is antagonized by a naturally-occurring lipoxin, that natural lipoxin is the corresponding lipoxin.

"Active region" shall mean the region of a natural lipoxin or lipoxin analog, which is associated with in vivo cellular interactions. The active region may bind the "recognition site" of a cellular lipoxin receptor or a macromolecule or complex of macromolecules, including an enzyme and its cofactor. Lipoxin $A_4$ analogs of the invention have an active region comprising $C_5$-$C_{15}$ of natural lipoxin $A_4$. Llipoxin $B_4$ analogs have an active region comprising C5-C14 of natural lipoxin B4.

The term "recognition site" or receptor is art-recognized and is intended to refer generally to a functional macromolecule or complex of macromolecules with which certain groups of cellular messengers, such as hormones, leukotrienes, and lipoxins, must first interact before the biochemical and physiological responses to those messengers are initiated. As used in this application, a receptor may be isolated, on an intact or permeabilized cell, or in tissue, including an organ. A receptor may be from or in a living subject, or it may be cloned. A receptor may normally exist or it may be induced by a disease state, by an injury, or by artificial means. A compound of this invention may bind reversibly, irreversibly, competitively, noncompetitively, or uncompetitively with respect to the natural substrate of a recognition site.

The term "metabolic transformation region" is intended to refer generally to that portion of a lipoxin, a lip ox in metabolite, or lipoxin analog including a lipoxin analog metabolite, upon which an enzyme or an enzyme and its cofactor attempts to perform one or more metabolic transformations which that enzyme or enzyme and cofactor normally transform on lipoxins. The metabolic transformation region may or may not be susceptible to the transformation. A nonlimiting example of a metabolic transformation region of a lipoxin is a portion of $LXA_4$ that includes the C-13,14 double bond or the C-15 hydroxyl group, or both.

The term "detectable label molecule" is meant to include fluorescent, phosphorescent, and radiolabeled molecules used to trace, track, or identify the compound or receptor recognition site to which the detectable label molecule is bound. The label molecule may be detected by any of the several methods known in the art.

The term "labeled lipoxin analog" is further understood to encompass compounds which are labeled with radioactive isotopes, such as but not limited to tritium ($^3H$), deuterium ($^2H$), carbon ($^{14}C$), or otherwise labeled (e.g. fluorescently). The compounds of this invention may be labeled or derivatized, for example, for kinetic binding experiments, for further elucidating metabolic pathways and enzymatic mechanisms, or for characterization by methods known in the art of analytical chemistry.

The term "inhibits metabolism" means the blocking or reduction of activity of an enzyme which metabolizes a native lipoxin. The blockage or reduction may occur by covalent bonding, by irreversible binding, by reversible binding which has a practical effect of irreversible binding, or by any other means which prevents the enzyme from operating in its usual manner on another lipoxin analog, including a lipoxin analog metabolite, a lipoxin, or a lipoxin metabolite.

The term "resists metabolism" is meant to include failing to undergo one or more of the metabolic degradative transformations by at least one of the enzymes which metabolize lipoxins. Two nonlimiting examples of $LXA_4$ analog that resists metabolism are 1) a structure which can not be oxidized to the 15-oxo form, and 2) a structure which may be oxidized to the 15-oxo form, but is not susceptible to enzymatic reduction to the 13,14-dihydro form.

The term "more slowly undergoes metabolism" means having slower reaction kinetics, or requiring more time for the completion of the series of metabolic transformations by one or more of the enzymes which metabolize lipoxin. A nonlimiting example of a $LXA_4$ analog which more slowly undergoes metabolism is a structure which has a higher transition state energy for C-15 dehydrogenation than does $LXA_4$ because the analog is sterically hindered at the C-16.

The term "tissue" is intended to include intact cells, blood, blood preparations such as plasma and serum, bones, joints, muscles, smooth muscles, and organs.

The term "halogen" is meant to include fluorine, chlorine, bromine and iodine, or fluoro, chloro, bromo, and iodo. In certain aspects, the compounds of the invention do not include halogenated compounds, e.g., fluorinated compounds.

The term "subject" is intended to include living organisms susceptible to conditions or diseases caused or contributed to by inflammation, asthma, asthma related disorders of the respiratory tract and lung, or disorders of the respiratory tract and lung as generally disclosed, but not limited to, throughout this specification. Examples of subjects include humans, dogs, cats, cows, goats, and mice. The term subject is further intended to include transgenic species.

When the compounds of the present invention are administered as pharmaceuticals, to humans and mammals, they can be given per se or as a pharmaceutical composition containing, for example, 0.1 to 99.5% (more preferably, 0.5 to 90%) of active ingredient in combination with a pharmaceutically acceptable carrier.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting a compound(s) of the present invention within or to the subject such that it can perform its intended function. Typically, such compounds are carried or transported from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; phosphate buffer solutions; and other non-toxic compatible substances employed in pharmaceutical formulations.

In certain embodiment, the compounds of the present invention may contain one or more acidic functional groups and, thus, are capable of forming pharmaceutically acceptable salts with pharmaceutically acceptable bases. The term "pharmaceutically acceptable salts, esters, amides, and prodrugs" as used herein refers to those carboxylate salts, amino acid addition salts, esters, amides, and prodrugs of the compounds of the present invention which are, within the scope of sound medical judgment, suitable for use in contact with the tissues of patients without undue toxicity, irritation, allergic response, and the like, commensurate with a reasonable benefit/risk ratio, and effective for their intended use of the compounds of the invention. The term "salts" refers to the relatively non-toxic, inorganic and organic acid addition salts of compounds of the present invention. These salts can be prepared in situ during the final isolation and purification of the compounds or by separately reacting the purified compound in its free base form with a suitable organic or inorganic acid and isolating the salt thus formed. These may include cations based on the alkali and alkaline earth metals, such as sodium, lithium, potassium, calcium, magnesium and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine, and the like. (See, for example, Berge S. M., et al., "Pharmaceutical Salts," J. Pharm. Sci., 1977; 66:1-19 which is incorporated herein by reference).

The term "pharmaceutically acceptable esters" refers to the relatively non-toxic, esterified products of the compounds of the present invention. These esters can be prepared in situ during the final isolation and purification of the compounds, or by separately reacting the purified compound in its free acid form or hydroxyl with a suitable esterifying agent. Carboxylic acids can be converted into esters via treatment with an alcohol in the presence of a catalyst. The term is further intended to include lower hydrocarbon groups capable of being solvated under physiological conditions, e.g., alkyl esters, methyl, ethyl and propyl esters. In certain embodiments, the ester is not a methyl ester (See, for example, Berge et al., supra.).

Wetting agents, emulsifiers and lubricants, such as sodium lauryl sulfate and magnesium stearate, as well as coloring agents, release agents, coating agents, sweetening, flavoring and perfuming agents, preservatives and antioxidants can also be present in the compositions.

Examples of pharmaceutically acceptable antioxidants include: water soluble antioxidants, such as ascorbic acid, cysteine hydrochloride, sodium bisulfate, sodium metabisulfite, sodium sulfite and the like; oil-soluble antioxidants, such as ascorbyl palmitate, butylated hydroxyanisole (BHA), butylated hydroxytoluene (BHT), lecithin, propyl gallate, alpha-tocopherol, and the like; and metal chelating agents, such as citric acid, ethylenediamine tetraacetic acid (EDTA), sorbitol, tartaric acid, phosphoric acid, and the like.

Formulations of the present invention include those suitable for intravenous, oral, nasal, topical, transdermal, buccal, sublingual, rectal, vaginal and/or parenteral administration. The formulations may conveniently be presented in unit dosage form and may be prepared by any methods well known in the art of pharmacy. The amount of active ingredient which can be combined with a carrier material to produce a single dosage form will generally be that amount of the compound which produces a therapeutic effect. Generally, out of one hundred per cent, this amount will range from about 1 per cent to about ninety-nine percent of active ingredient, preferably from about 5 per cent to about 70 per cent, most preferably from about 10 per cent to about 30 per cent.

Methods of preparing these formulations or compositions include the step of bringing into association a compound of the present invention with the carrier and, optionally, one or more accessory ingredients. In general, the formulations are prepared by uniformly and intimately bringing into association a compound of the present invention with liquid carriers, or finely divided solid carriers, or both, and then, if necessary, shaping the product.

Formulations of the invention suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia) and/or as mouth washes and the like, each containing a predetermined amount of a compound of the present invention as an active ingredient. A compound of the present invention may also be administered as a bolus, electuary or paste.

In solid dosage forms of the invention for oral administration (capsules, tablets, pills, dragees, powders, granules and the like), the active ingredient is mixed with one or more pharmaceutically acceptable carriers, such as sodium citrate or dicalcium phosphate, and/or any of the following: fillers or extenders, such as starches, lactose, sucrose, glucose, mannitol, and/or silicic acid; binders, such as, for example, carboxymethylcellulose, alginates, gelatin, polyvinyl pyrrolidone, sucrose and/or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such a talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the powdered compound moistened with an inert liquid diluent.

The tablets, and other solid dosage forms of the pharmaceutical compositions of the present invention, such as dragees, capsules, pills and granules, may optionally be scored or prepared with coatings and shells, such as enteric coatings and other coatings well known in the pharmaceutical-formulating art. They may also be formulated so as to provide slow or controlled release of the active ingredient therein using, for example, hydroxypropylmethyl cellulose in varying proportions to provide the desired release profile, other polymer matrices, liposomes and/or microspheres. They may be sterilized by, for example, filtration through a bacteria-retaining filter, or by incorporating sterilizing agents in the form of sterile solid compositions which can be dissolved in sterile water, or some other sterile injectable medium immediately before use. These compositions may also optionally contain opacifying agents and may be of a composition that they release the active ingredient(s) only, or preferentially, in a certain portion of the gastrointestinal tract, optionally, in a delayed manner. Examples of embedding compositions which can be used include polymeric substances and waxes. The active ingredient can also be in micro-encapsulated form, if appropriate, with one or more of the above-described excipients.

Liquid dosage forms for oral administration of the compounds of the invention include pharmaceutically acceptable emulsions, microemulsions, solutions, suspensions, syrups and elixirs. In addition to the active ingredient, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, coloring, perfuming and preservative agents.

Suspensions, in addition to the active compounds, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations of the pharmaceutical compositions of the invention for rectal or vaginal administration may be presented as a suppository, which may be prepared by mixing one or more compounds of the invention with one or more suitable nonirritating excipients or carriers comprising, for example, cocoa butter, polyethylene glycol, a suppository wax or a salicylate, and which is solid at room temperature, but liquid at body temperature and, therefore, will melt in the rectum or vaginal cavity and release the active compound.

Formulations of the present invention which are suitable for vaginal administration also include pessaries, tampons, creams, gels, pastes, foams or spray formulations containing such carriers as are known in the art to be appropriate.

Dosage forms for the topical or transdermal administration of a compound of this invention include powders, sprays, ointments, pastes, creams, lotions, gels, solutions, patches and inhalants. The active compound may be mixed under sterile conditions with a pharmaceutically acceptable carrier, and with any preservatives, buffers, or propellants which may be required.

The ointments, pastes, creams and gels may contain, in addition to an active compound of this invention, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Transdermal patches have the added advantage of providing controlled delivery of a compound of the present invention to the body. Such dosage forms can be made by dissolving or dispersing the compound in the proper medium. Absorption enhancers can also be used to increase the flux of the compound across the skin. The rate of such flux can be controlled by either providing a rate controlling membrane or dispersing the active compound in a polymer matrix or gel.

Ophthalmic formulations, eye ointments, powders, solutions and the like, are also contemplated as being within the scope of this invention.

Pharmaceutical compositions of this invention suitable for parenteral administration comprise one or more compounds of the invention in combination with one or more pharmaceutically acceptable sterile isotonic aqueous or nonaqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

In some cases, in order to prolong the effect of a drug, it is desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form. Alternatively, delayed absorption of a parenterally-administered drug form is accomplished by dissolving or suspending the drug in an oil vehicle.

Injectable depot forms are made by forming microencapsule matrices of the subject compounds in biodegradable polymers such as polylactide-polyglycolide. Depending on the ratio of drug to polymer, and the nature of the particular polymer employed, the rate of drug release can be controlled. Examples of other biodegradable polymers include poly (orthoesters) and poly(anhydrides). Depot injectable formulations are also prepared by entrapping the drug in liposomes or microemulsions which are compatible with body tissue.

The preparations of the present invention may be given orally, parenterally, topically, or rectally. They are of course given by forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Intravenous injection administration is preferred.

The phrases "parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systematically," "peripheral administration" and "administered peripherally" as used herein mean the administration of a compound, drug or other material other than directly into the central nervous system, such that it enters the patient's system and, thus, is subject to metabolism and other like processes, for example, subcutaneous administration.

These compounds may be administered to humans and other animals for therapy by any suitable route of administration, including orally, nasally, as by, for example, a spray, rectally, intravaginally, parenterally, intracisternally and topically, as by powders, ointments or drops, including buccally and sublingually.

Regardless of the route of administration selected, the compounds of the present invention, which may be used in a suitable hydrated form, and/or the pharmaceutical compositions of the present invention, are formulated into pharmaceutically acceptable dosage forms by conventional methods known to those of ordinary skill in the art.

Actual dosage levels of the active ingredients in the pharmaceutical compositions of this invention may be varied so as to obtain an amount of the active ingredient which is effective to achieve the desired therapeutic response for a particular patient, composition, and mode of administration, without being toxic to the patient.

The selected dosage level will depend upon a variety of factors including the activity of the particular compound of the present invention employed, or the ester, salt or amide thereof, the route of administration, the time of administration, the rate of excretion of the particular compound being employed, the duration of the treatment, other drugs, compounds and/or materials used in combination with the particular compound employed, the age, sex, weight, condition, general health and prior medical history of the patient being treated, and like factors well known in the medical arts.

A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In general, a suitable daily dose of a compound of the invention will be that amount of the compound which is the lowest dose effective to produce a therapeutic effect. Such an effective dose will generally depend upon the factors described above. Generally, intravenous and subcutaneous doses of the compounds of this invention for a patient, when used for the indicated analgesic effects, will range from about 0.0001 to about 100 mg per kilogram of body weight per day, more preferably from about 0.01 to about 50 mg per kg per day, and still more preferably from about 0.1 to about 40 mg per kg per day. For example, between about 0.01 microgram and 20 micrograms, between about 20 micrograms and 100 micrograms and between about 10 micrograms and 200 micrograms of the compounds of the invention are administered per 20 grams of subject weight.

If desired, the effective daily dose of the active compound may be administered as two, three, four, five, six or more sub-doses administered separately at appropriate intervals throughout the day, optionally, in unit dosage forms.

Delivery of the lipoxin analogs of the present invention to the lung by way of inhalation is an important method of treating a variety of respiratory conditions noted throughout the specification, including such common local conditions as bronchial asthma and chronic obstructive pulmonary disease. The lipoxin analogs can be administered to the lung in the form of an aerosol of particles of respirable size (less than about 10 µm in diameter). The aerosol formulation can be presented as a liquid or a dry powder. In order to assure proper particle size in a liquid aerosol, as a suspension, particles can be prepared in respirable size and then incorporated into the suspension formulation containing a propellant. Alternatively, formulations can be prepared in solution form in order to avoid the concern for proper particle size in the formulation. Solution formulations should be dispensed in a manner that produces particles or droplets of respirable size.

Once prepared an aerosol formulation is filled into an aerosol canister equipped with a metered dose valve. The formulation is dispensed via an actuator adapted to direct the dose from the valve to the subject.

Formulations of the invention can be prepared by combining (i) at least one lipoxin analog in an amount sufficient to provide a plurality of therapeutically effective doses; (ii) the water addition in an amount effective to stabilize each of the formulations; (iii) the propellant in an amount sufficient to propel a plurality of doses from an aerosol canister; and (iv) any further optional components e.g. ethanol as a cosolvent; and dispersing the components. The components can be dispersed using a conventional mixer or homogenizer, by shaking, or by ultrasonic energy. Bulk formulation can be transferred to smaller individual aerosol vials by using valve to valve transfer methods, pressure filling or by using conventional cold-fill methods. It is not required that a stabilizer used in a suspension aerosol formulation be soluble in the propellant. Those that are not sufficiently soluble can be coated onto the drug particles in an appropriate amount and the coated particles can then be incorporated in a formulation as described above.

Aerosol canisters equipped with conventional valves, preferably metered dose valves, can be used to deliver the formulations of the invention. Conventional neoprene and buna valve rubbers used in metered dose valves for delivering conventional CFC formulations can be used with formulations containing HFC-134a or HFC-227. Other suitable materials include nitrile rubber such as DB-218 (American Gasket and Rubber, Schiller Park, Ill.) or an EPDM rubber such as VISTALON® (Exxon), ROYALEN (UniRoyal), or BUNA EP (Bayer). Also suitable are diaphragms fashioned by extrusion, injection molding or compression molding from a thermoplastic elastomeric material such as FLEXOMER® GERS 1085 NT polyolefin (Union Carbide).

Formulations of the invention can be contained in conventional aerosol canisters, coated or uncoated, anodized or unanodized, e.g., those of aluminum, glass, stainless steel, polyethylene terephthalate.

The formulation(s) of the invention can be delivered to the respiratory tract and/or lung by oral inhalation in order to effect bronchodilation or in order to treat a condition susceptible of treatment by inhalation, e.g., asthma, chronic obstructive pulmonary disease, etc. as described throughout the specification.

The formulations of the invention can also be delivered by nasal inhalation as known in the art in order to treat or prevent the respiratory conditions mentioned throughout the specification.

While it is possible for a compound of the present invention to be administered alone, it is preferable to administer the compound as a pharmaceutical composition.

The invention features an article of manufacture that contains packaging material and a lipoxin formulation contained within the packaging material. This formulation contains an at least one lipoxin analog and the packaging material contains a label or package insert indicating that the formulation can be administered to the subject to treat one or more respiratory conditions, in an amount, at a frequency, and for a duration effective to treat or prevent such respiratory condition(s). Such conditions are mentioned throughout the specification and are incorporated herein by reference.

More specifically, the invention features an article of manufacture that contains packaging material and a lipoxin formulation contained within the packaging material. This formulation contains at least one lipoxin analog. The packaging material contains a label or package insert indicating that the formulation can be administered to the subject to asthma in an amount, at a frequency, and for a duration effective treat or prevent asthma symptoms.

METHODS

Sensitization and challenge protocols. Five to seven week old male BALB/c (Charles River Laboratories, Wilmington, Mass.) or female hCD11b-hALX FvB transgenic mice were housed in isolation cages under viral antibody-free conditions. After Harvard Medical Area IRB approval (Protocol #02570), mice were sensitized with intraperitoneal injections of ovalbumin (OVA) (Grade III; Sigma Chemical Co., St. Louis, Mo.) (10 μg) plus 1 mg aluminum hydroxide (ALUM) (J.T. Baker Chemical Co.; Phillipsburg, N.J.) as adjuvant in 0.2 ml PBS on days 0 and 7. On days 14, 15, 16 and 17, the mice received 10 μg/mouse of an analog (ref. 16) of $LXA_4$ (15-epi,16-para-fluoro-phenoxy-$LXA_4$-methyl ester, LXa) or PBS with 1.6 mM $CaCl_2$ and 1.6 mM $MgCl_2$ (0.1 ml) by intravenous injection at least 1 h prior to an aerosol challenge containing either PBS or 6% OVA for 25 min/day. The analog was designed to resist rapid enzymatic inactivation and was based on the structure of the aspirin-triggered 15-epi-$LXA_4$ (ref. 16), which carries its carbon 15 position alcohol in the R configuration or epimeric (R) to native $LXA_4$. On day 18, 24 h after the last aerosol challenge, airway responsiveness to intravenous methacholine (33-1000 μg/kg) was measured, bilateral bronchoalveolar lavage (BAL) (2 aliquots of 1 ml PBS plus 0.6 mM EDTA) was performed and tissues (whole blood, lungs, mediastinal lymph nodes and spleen) were harvested for histological analysis. Lung resistance ($R_L$) was measured using a sealed constant mass plethysmograph. The effective dose of methacholine required to increase $R_L$ to 200% of control values was defined as the $ED_{200}$ and used as an index of airway responsiveness (as in refs. 14, 15). For mice studied using a whole body plethysmograph to assess airway responsiveness (Buxco), each mouse was placed into a chamber and box pressure/time waveform was analyzed to yield the indicator of airflow obstruction, enhanced pause (Penh). PBS or methacholine (100 mg/ml) was given by aerosol through an inlet of the chamber for 4.5 min. Readings were initiated at 3 min and continued for 12 min. Peak and one min average Penh values were determined. Serum total IgE levels were determined by ELISA (Crystal Chem, Chicago, Ill.). In situ hybridization of murine ALX was performed using an anti-sense oligonucleotide probe (534 bp in length) corresponding to nucleic acids +581-+1115 (GenBank Accession No. NM008042) with the assistance of the Dana-Farber/Harvard Cancer Center Pathology Core Facility (under the direction of Dr. Massimo Loda).

Allergen-initiated respiratory inflammation. Measurement of inflammatory mediators was determined in cell-free BAL fluid (2000 g, 10 min) by sensitive and specific ELISA's, in tandem, for interleukin-5 (IL-5), IL-13, eotaxin, tumor necrosis factor (TNFα) (R&D Systems, Minneapolis, Minn.), $LTB_4$, cysteinyl LT, $PGE_2$ (Cayman Chemical Co., Ann Arbor, Mich.), and $LXA_4$ (Neogen, Lexington, Ky.). Cells were resuspended in HBSS, enumerated by hemocytometer, and concentrated onto microscope slides by cytocentrifuge (STATspin) (265 g). Cells were stained with a Wright-Giemsa stain (Sigma Chemical Co.) to determine leukocyte differentials (after counting ≧200 cells).

Eosinophil tissue infiltration. Five minutes after topical delivery of LXa (10 μg in 10 μl acetone) or vehicle control, $PGE_2$ (1 μg, Cayman Chemical Co.) plus $LTB_4$ (1 μg, Cayman Chemical Co.) were topically applied employing 10 μl acetone that rapidly evaporates to the inside of left and right ears of male mice (hCD11b-hALX FvB transgenic, hCD11b-hBLT FvB transgenic[36] or age and gender-matched non-transgenic littermates; 4-5 months old, ~30 g body weight). After 13-16 h, 6 mm diameter skin punch biopsies (Acu-Punch, Fisher Scientific, Pittsburgh, Pa.) were obtained. Samples were sliced finely with scalpels, homogenized in 400 μl of potassium phosphate buffer (pH 6.0) containing 0.5% hexadecyltrimethylammonium bromide, followed by three cycles of sonication and freeze-thaw. The particulate matter was removed by centrifugation (16,000 g for 20 min) and resulting supernatants were assayed for eosinophil peroxidase (EPO) activity as in ref. 37. Briefly, 3-(4-hydroxyphenyl)propionic acid (HPA, Aldrich, Milwaukee, Wis.) (100 μM) was exposed (10 min, 37° C.) to partially purified EPO (~75-150 μg extracted ear skin protein) in the presence of NaBr (100 μM). EPO activity was monitored by monobromination of HPA (Br-HPA). To extract Br-HPA, tissue samples were spiked with an internal standard (L-tyrosine (ring)-$d_4$, Cambridge Isotopes, Andover, Mass.), loaded onto C18 SepPak cartridges (Waters, Milford, Mass.) for extraction in 0.1% TFA, eluted with MeOH:$dH_2O$ (1:1, v/v)+0.1% TFA, brought to dryness in vacuo (rotoevaporation) and derivatized (overnight) with BSTFA (Pierce, Rockford, Ill.). Trimethyl silylated HPA, Br-HPA and $d_4$-tyrosine were detected by GC-MS (GC model #6890, MS model #5973, Hewlett Packard, San Fernando, Calif.). HPA-TMS had a retention time of 7.01 min with diagnostic molecular ion ($M^+$=310) and mass fragmentation, including m/z 295 [$M^+$ —$CH_3$], m/z 192 [$M^+$ —COOTMS], and a base peak of m/z 179 [$M^+$ —$CH_2$COOTMS]. Br-HPA-TMS had a retention time of 9.30 min with diagnostic molecular ion ($M^+$=390) and mass fragmentation, including m/z 375 [$M^+$ —$CH_3$], m/z 272 [$M^+$ —COOTMS], and a base peak of m/z 259 [$M^+$ —$CH_2$COOTMS]. In addition, the mass spectrum of Br-HPA demonstrated the isotopic pattern of a monobrominated species. EPO activity was quantitated by percent conversion of HPA to Br-HPA, taking into account the recovery of the internal standard (>80%) and normalized for the samples' protein content (determined by BioRad protein reagent) (Bio-Rad, Hercules, Calif.).

TABLE I

| Eicosanoid | Levels (pg/ml) | BAL Samples (n) |
| --- | --- | --- |
| $PGE_2$ | 1117.7 ± 103.8 | 5 |
| CysLT | 139.0 ± 27.3 | 9 |
| $LTB_4$ | 6.4 ± 2.3 | 9 |
| $LXA_4$ | 15.0 ± 3.3 | 5 |

*Mice were sensitized to OVA and challenged daily with an aerosol of 6% OVA for 4 consecutive days (see Methods). BAL was performed 24 h after the final OVA aerosol. After centrifugation, eicosanoid levels were determined using ELISA's with the cell-free BAL supernatants. Values are the mean (pg/ml) of duplicate determinations.

REFERENCES

1. Leff, A. R. Role of Leukotrienes in Bronchial Hyperresponsiveness and Cellular Responses in Airways. *American Journal of Respiratory and Critical Care Medicine* 161, S125-S132 (2000).

2. Bousquet, J., Jeffery, P. K., Busse, W. W., Johnson, M. & Vignola, A. M. Asthma. From bronchoconstriction to airways inflammation and remodeling. *American Journal of Respiratory and Critical Care Medicine* 161, 1720-45 (2000).
3. Robinson, D. S. et al. Predominant TH2-like bronchoalveolar T-lymphocyte population in atopic asthma. *New England Journal of Medicine* 326, 298-304 (1992).
4. Broide, D. H. et al. Cytokines in symptomatic asthma airways. *J Allergy Clin Immunol* 89, 958-967 (1992).
5. Samuelsson, B. From studies of biochemical mechanisms to novel biological mediators: prostaglandin endoperoxides, thromboxanes and leukotrienes. in *Les Prix Nobel: Nobel Prizes, Presentations, Biographies and Lectures* 153-174 (Almqvist & Wiksell, Stockholm, 1982).
6. Drazen, J. M., Israel, E. & O'Byrne, P. M. Treatment of asthma with drugs modifying the leukotriene pathway. *New England Journal of Medicine* 340, 197-206 (1999).
7. Serhan, C. N., Haeggstrom, J. Z. & Leslie, C. C. Lipid mediator networks in cell signaling: update and impact of cytokines. *FASEB Journal* 10, 1147-58 (1996).
8. McMahon, B., Mitchell, S., Brady, H. R. & Godson, C. Lipoxins: revelations on resolution. *Trends in Pharmacological Sciences* 22, 391-5 (2001).
9. Levy, B. D., Clish, C. B., Schmidt, B., Gronert, K. & Serhan, C. N. Lipid mediator class switching during acute inflammation: signals in resolution. *Nature Immunology* 2, 612-9 (2001).
10. Lee, T. H. et al. Identification of lipoxin A4 and its relationship to the sulfidopeptide leukotrienes C4, D4, and E4 in the bronchoalveolar lavage fluids obtained from patients with selected pulmonary diseases. *American Review of Respiratory Disease* 141, 1453-8 (1990).
11. Badr, K. F., DeBoer, D. K., Schwartzberg, M. & Serhan, C. N. Lipoxin A4 antagonizes cellular and in vivo actions of leukotriene D4 in rat glomerular mesangial cells: evidence for competition at a common receptor. *Proceedings of the National Academy of Sciences of the United States of America* 86, 3438-42 (1989).
12. Gronert, K., Martinsson-Niskanen, T., Ravasi, S., Chiang, N. & Serhan, C. N. Selectivity of recombinant human leukotriene $D_4$, leukotriene $B_4$, and lipoxin A4 receptors with aspirin-triggered 15-epi-$LXA_4$ and regulation of vascular and inflammatory responses. *American Journal of Pathology* 158, 3-9 (2001).
13. Takano, T. et al. Aspirin-triggered 15-epi-lipoxin A4 (LXA4) and LXA4 stable analogues are potent inhibitors of acute inflammation: evidence for anti-inflammatory receptors. Journal of Experimental Medicine 185, 1693-704 (1997).
14. De Sanctis, G. T. et al. Interleukin-8 receptor modulates IgE production and B-cell expansion and trafficking in allergen-induced pulmonary inflammation. *Journal of Clinical Investigation* 103, 507-15 (1999).
15. De Sanctis, G. T. et al. Contribution of nitric oxide synthases 1, 2, and 3 to airway hyperresponsiveness and inflammation in a murine model of asthma. *Journal of Experimental Medicine* 189, 1621-30 (1999).
16. Clish, C. B. et al. Local and systemic delivery of a stable aspirin-triggered lipoxin prevents neutrophil recruitment in vivo. *Proceedings of the National Academy of Sciences of the United States of America* 96, 8247-52 (1999).
17. Omitted.
18. Holgate, S. T. The epidemic of allergy and asthma. *Nature* 402, B2-4 (1999).
19. Drazen, J. M., Silverman, E. K. & Lee, T. H. Heterogeneity of therapeutic responses in asthma. *British Medical Bulletin* 56, 1054-70 (2000).
20. Bryan, S. A. et al. Effects of recombinant human interleukin-12 on eosinophils, airway hyper-responsiveness, and the late asthmatic response. *Lancet* 356, 2149-53 (2000).
21. Leckie, M. J. et al. Effects of an interleukin-5 blocking monoclonal antibody on eosinophils, airway hyper-responsiveness, and the late asthmatic response. *Lancet* 356, 2144-8 (2000).
22. Christie, P. E., Spur, B. W. & Lee, T. H. The effects of lipoxin A4 on airway responses in asthmatic subjects. *American Review of Respiratory Disease* 145, 1281-4 (1992).
23. Dahlen, S. E. et al. Actions of lipoxin A4 and related compounds in smooth muscle preparations and on the microcirculation in vivo. *Advances in Experimental Medicine & Biology* 229, 107-30 (1988).
24. Venkayya, R. et al. The Th2 lymphocyte products IL-4 and IL-13 rapidly induce airway hyperresponsiveness through direct effects on resident airway cells. *American Journal of Respiratory Cell & Molecular Biology* 26, 202-8 (2002).
25. Laporte, J. C. et al. Direct effects of interleukin-13 on signaling pathways for physiological responses in cultured human airway smooth muscle cells. *American Journal of Respiratory & Critical Care Medicine* 164, 141-8 (2001).
26. Cowburn, A. S., Holgate, S. T. & Sampson, A. P. IL-5 increases expression of 5-lipoxygenase-activating protein and translocates 5-lipoxygenase to the nucleus in human blood eosinophils. *Journal of Immunology* 163, 456-65 (1999).
27. Hisada, T., Salmon, M., Nasuhara, Y. & Chung, K. F. Cysteinyl-leukotrienes partly mediate eotaxin-induced bronchial hyperresponsiveness and eosinophilia in IL-5 transgenic mice. *American Journal of Respiratory & Critical Care Medicine* 160, 571-5 (1999).
28. Drazen, J. M. Leukotrienes as mediators of airway obstruction. *American Journal of Respiratory & Critical Care Medicine* 158, S193-200 (1998).
29. Resnati, M. et al. The fibrinolytic receptor for urokinase activates the G-protein-coupled chemotactic receptor FPRL1/LXA4R. *Proceedings of the National Academy of Sciences* 99, 1359-1364 (2002).
30. Soyombo, O., Spur, B. W. & Lee, T. H. Effects of lipoxin A4 on chemotaxis and degranulation of human eosinophils stimulated by platelet-activating factor and N-formyl-L-methionyl-L-leucyl-L-phenylalanine. *Allergy* 49, 230-4 (1994).
31. Bandeira-Melo, C. et al. Cutting edge: lipoxin (LX) A4 and aspirin-triggered 15-epi-LXA4 block allergen-induced eosinophil trafficking. *Journal of Immunology* 164, 2267-71 (2000).
32. Bandeira-Melo, C. et al. Cyclooxygenase-2-derived prostaglandin $E_2$ and lipoxin $A_4$ accelerate resolution of allergic edema in Angiostrongylus costaricensis-infected rats: relationship with concurrent eosinophilia. *Journal of Immunology* 164, 1029-36 (2000).
33. Aliberti, J., Hieny, S., Reis e Sousa, C., Serhan, C. N. & Sher, A. Lipoxin-mediated inhibition of IL-12 production by DCs: a mechanism for regulation of microbial immunity. *Nature Immunology* 3, 76-82 (2002).
34. Sanak, M. et al. Aspirin-tolerant asthmatics generate more lipoxins than aspirin-intolerant asthmatics. *European Respiratory Journal* 16, 44-9 (2000).

35. Godson, C. et al. Cutting edge: lipoxins rapidly stimulate nonphlogistic phagocytosis of apoptotic neutrophils by monocyte-derived macrophages. *Journal of Immunology* 164, 1663-7 (2000).
36. Chiang, N. et al. Leukotriene $B_4$ receptor transgenic mice reveal novel protective roles for lipoxins and aspirin-triggered lipoxins in reperfusion. *Journal of Clinical Investigation* 104, 309-16 (1999).
37. Wu, W. et al. Eosinophils generate brominating oxidants in allergen-induced asthma. *Journal of Clinical Investigation* 105, 1455-63 (2000).

One having ordinary skill in the art will appreciate further features and advantages of the invention based on the above-described embodiments. Accordingly, the invention is not to be limited by what has been particularly shown and described, except as indicated by the appended claims. All publications and references cited herein, including those in the background section, are expressly incorporated herein by reference in their entirety.

What is claimed is:

1. A method for treating airway hyper-responsiveness comprising the step of administering to a subject in need thereof, a therapeutically effective amount of a lipoxin analog having the formula

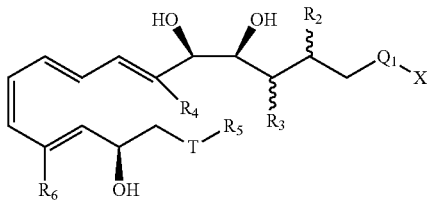

wherein X is $R_1$, $OR_1$, or $SR_1$;
wherein $R_1$ is
  (i) a hydrogen atom;
  (ii) an alkyl of 1 to 8 carbon atoms, inclusive, which may be straight chain or branched;
  (iii) a cycloalkyl of 3 to 10 carbon atoms;
  (iv) an aralkyl of 7 to 12 carbon atoms;
  (v) phenyl;
  (vi) substituted phenyl

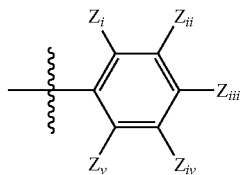

wherein $Z_i$, $Z_{ii}$, $Z_{iii}$, $Z_{iv}$ and $Z_v$ are each independently selected from $-NO_2$, $-CN$, $-C(=O)-R_1$, $-SO_3H$, a hydrogen atom, halogen, methyl, $-OR_x$, wherein $R_x$ is 1 to 8 carbon atoms, inclusive, which may be a straight chain or branched, and hydroxyl;
  (vii) a detectable label molecule; or
  (viii) a straight or branched chain alkenyl of 2 to 8 carbon atoms, inclusive;
wherein $Q_1$ is (C=O), $SO_2$ or (CN), provided when $Q_1$ is CN, then X is absent;
wherein one of $R_2$ and $R_3$ is a hydrogen atom and the other is
  (a) H;
  (b) an alkyl of 1 to 8 carbon atoms, inclusive, which may be a straight chain or branched;
  (c) a cycloalkyl of 3 to 6 carbon atoms, inclusive;
  (d) an alkenyl of 2 to 8 carbon atoms, inclusive, which may be straight chain or branched; or
  (e) $R_aQ_2R_b$ wherein $Q_2$ is $-O-$ or $-S-$; wherein $R_a$ is alkylene of 0 to 6 carbon atoms, inclusive, which may be straight chain or branched and wherein $R_b$ is alkyl of 0 to 8 carbon atoms, inclusive, which may be straight chain or branched, provided when $R_b$ is 0, then $R_b$ is a hydrogen atom;
wherein $R_4$ is
  (a) H;
  (b) an alkyl of 1 to 6 carbon atoms, inclusive, which may be a straight chain or branched;
wherein $R_5$ is

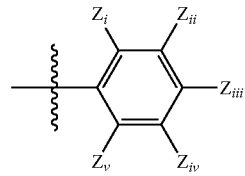

wherein $Z_i$, $Z_{ii}$, $Z_{iii}$, $Z_{iv}$ and $Z_v$ are each independently selected from $-NO_2$, $-CN$, $-C(=O)-R_1$, $-SO_3H$, a hydrogen atom, halogen, methyl, $-OR_x$, wherein $R_x$ is 1 to 8 carbon atoms, inclusive, which may be a straight chain or branched, and hydroxyl or a substituted or unsubstituted, branched or unbranched alkyl group;
wherein $R_6$ is
  (a) H;
  (b) an alkyl from 1 to 4 carbon atoms, inclusive, straight chain or branched;
wherein T is O or S, and pharmaceutically acceptable salts thereof.

* * * * *